(12) United States Patent
Sun et al.

(10) Patent No.: US 11,090,255 B2
(45) Date of Patent: *Aug. 17, 2021

(54) USE OF POLYCARBOXYLIC ACID COMPOUNDS FOR THE TREATMENT OF FIBRIOUS AMINO ACID BASED SUBSTRATES, ESPECIALLY HAIR

(71) Applicant: Momentive Performance Materials, Inc., Waterford, NY (US)

(72) Inventors: Kunshan Sun, Millwood, NY (US); Anne Dussaud, Tarrytown, NY (US); Nicholas Stasiak, Putnam Valley, NY (US); Katharina Streicher, Leverkusen (DE); Roland Wagner, Bonn (DE)

(73) Assignee: Momentive Performance Materials Inc., Waterford, NY (US)

( * ) Notice: Subject to any disclaimer, the term of this patent is extended or adjusted under 35 U.S.C. 154(b) by 145 days.

This patent is subject to a terminal disclaimer.

(21) Appl. No.: 16/208,872

(22) Filed: Dec. 4, 2018

(65) Prior Publication Data
US 2020/0170923 A1 Jun. 4, 2020

(51) Int. Cl.
| | |
|---|---|
| *C07C 69/34* | (2006.01) |
| *A61K 8/891* | (2006.01) |
| *A61K 8/362* | (2006.01) |
| *A61K 8/39* | (2006.01) |
| *A61K 8/41* | (2006.01) |
| *A61K 8/42* | (2006.01) |
| *A61K 8/86* | (2006.01) |
| *A61K 8/898* | (2006.01) |
| *A61K 8/899* | (2006.01) |
| *A61Q 5/00* | (2006.01) |
| *A61Q 5/06* | (2006.01) |
| *A61Q 5/12* | (2006.01) |
| *C07C 69/48* | (2006.01) |
| *C07C 69/44* | (2006.01) |
| *C08G 59/14* | (2006.01) |
| *C07C 69/38* | (2006.01) |
| *C07C 69/40* | (2006.01) |
| *C07C 69/46* | (2006.01) |
| *C07C 69/70* | (2006.01) |
| *C08G 59/18* | (2006.01) |
| *C07C 235/76* | (2006.01) |
| *C07C 69/42* | (2006.01) |
| *C08G 59/22* | (2006.01) |
| *C07C 69/36* | (2006.01) |
| *C07C 69/50* | (2006.01) |

(52) U.S. Cl.
CPC ............ *A61K 8/891* (2013.01); *A61K 8/362* (2013.01); *A61K 8/39* (2013.01); *A61K 8/416* (2013.01); *A61K 8/42* (2013.01); *A61K 8/86* (2013.01); *A61K 8/898* (2013.01); *A61K 8/899* (2013.01); *A61Q 5/004* (2013.01); *A61Q 5/06* (2013.01); *A61Q 5/12* (2013.01); *C07C 69/34* (2013.01); *C07C 69/36* (2013.01); *C07C 69/38* (2013.01); *C07C 69/40* (2013.01); *C07C 69/42* (2013.01); *C07C 69/44* (2013.01); *C07C 69/46* (2013.01); *C07C 69/48* (2013.01); *C07C 69/50* (2013.01); *C07C 69/70* (2013.01); *C07C 235/76* (2013.01); *C08G 59/1477* (2013.01); *C08G 59/186* (2013.01); *C08G 59/22* (2013.01)

(58) Field of Classification Search
CPC ......... C07C 69/34; C07C 69/36; C07C 69/38; C07C 69/40; C07C 69/42; C07C 69/44; C07C 69/46; C07C 69/48; C07C 69/50
See application file for complete search history.

(56) References Cited

U.S. PATENT DOCUMENTS

| | | | |
|---|---|---|---|
| 1,927,339 A | 9/1933 | Ernster | |
| 2,498,658 A * | 2/1950 | Keiser | C10G 33/06 516/189 |
| 2,997,462 A * | 8/1961 | Horst-Jurgen Kranse | C11D 1/008 510/475 |
| 3,558,741 A | 1/1971 | Holub et al. | |
| 3,674,835 A * | 7/1972 | Boehmke | C07C 69/92 560/64 |
| 4,075,167 A | 2/1978 | Takamizawa et al. | |
| 4,698,178 A | 10/1987 | Hüttinger et al. | |
| 4,833,225 A | 5/1989 | Schaefer et al. | |
| 4,891,166 A | 1/1990 | Schaefer et al. | |
| 4,891,168 A | 1/1990 | Schaefer et al. | |
| 4,931,062 A | 6/1990 | Bay et al. | |
| 4,981,485 A | 1/1991 | Motono | |
| 5,098,979 A | 3/1992 | O'Lenick, Jr. | |

(Continued)

FOREIGN PATENT DOCUMENTS

| | | |
|---|---|---|
| CA | 2092440 A1 | 3/1992 |
| CA | 2219541 A1 | 5/1998 |

(Continued)

OTHER PUBLICATIONS

English abstract (from SciFinder) JP U.S. Appl. No. 56/018,572, filed Apr. 1981.*

(Continued)

Primary Examiner — Margaret G Moore
(74) Attorney, Agent, or Firm — Joseph S. Ostroff

(57) ABSTRACT

This invention relates to the use of polycarboxylic acid compounds, aqueous compositions comprising the same, cosmetic compositions comprising the same, in particular, hair care compositions, and their use for the treatment of hair, and a process for the treatment of hair comprising the use of said cosmetic compositions.

5 Claims, No Drawings

(56) References Cited

U.S. PATENT DOCUMENTS

| | | | |
|---|---|---|---|
| 5,151,473 | A | 9/1992 | Herzig |
| 5,153,294 | A | 10/1992 | O'Lenick, Jr. |
| 5,166,297 | A | 11/1992 | O'Lenick, Jr. |
| 5,433,753 | A | 7/1995 | Dahmen et al. |
| 5,489,429 | A | 2/1996 | Griat et al. |
| 5,686,011 | A | 11/1997 | Lohmann et al. |
| 5,711,942 | A | 1/1998 | Eicken et al. |
| 5,801,270 | A * | 9/1998 | Uno ............... A61K 8/44 510/126 |
| 5,854,319 | A | 12/1998 | O'Lenick, Jr. et al. |
| 6,110,230 | A | 8/2000 | Friedrich et al. |
| 6,240,929 | B1 | 6/2001 | Richard et al. |
| 6,277,445 | B1 | 8/2001 | Hasegawa et al. |
| 6,379,751 | B1 | 4/2002 | Schafer et al. |
| 6,544,499 | B1 | 4/2003 | Glenn, Jr. et al. |
| 6,555,505 | B1 | 4/2003 | King et al. |
| 6,664,342 | B1 | 12/2003 | Köhler et al. |
| 6,730,766 | B2 | 5/2004 | Schattenmann et al. |
| 6,753,369 | B2 | 6/2004 | Hill, Jr. et al. |
| 7,041,767 | B2 | 5/2006 | Lange et al. |
| 7,148,327 | B2 | 12/2006 | Kelly et al. |
| 7,217,777 | B2 | 5/2007 | Lange et al. |
| 7,329,707 | B2 | 2/2008 | Sandner et al. |
| 7,563,856 | B2 | 7/2009 | Lange et al. |
| 7,563,857 | B2 | 7/2009 | Lange et al. |
| 9,144,537 | B1 | 9/2015 | Pressly et al. |
| 9,308,668 | B2 | 4/2016 | Delis et al. |
| 10,617,617 | B1 * | 4/2020 | Sun ............... C08G 59/1477 |
| 2001/0006654 | A1 | 7/2001 | Cannell et al. |
| 2005/0255073 | A1 | 11/2005 | Sockel et al. |
| 2006/0188456 | A1 | 8/2006 | Ferenz et al. |
| 2006/0255073 | A1 | 11/2006 | Sockel et al. |
| 2007/0048235 | A1 | 3/2007 | Harmalker et al. |
| 2007/0106045 | A1 | 5/2007 | Lange et al. |
| 2007/0129520 | A1 | 6/2007 | Ochs et al. |
| 2007/0287987 | A1 * | 12/2007 | Katsarava ............... A61L 27/58 604/502 |
| 2008/0027202 | A1 | 1/2008 | Ferenz et al. |
| 2008/0161500 | A1 | 7/2008 | Stark et al. |
| 2008/0213208 | A1 | 9/2008 | Moeller et al. |
| 2009/0000638 | A1 | 1/2009 | Wood et al. |
| 2009/0062459 | A1 | 3/2009 | Thum et al. |
| 2009/0076238 | A1 | 3/2009 | Lange et al. |
| 2009/0137764 | A1 | 5/2009 | Sutton et al. |
| 2009/0165812 | A1 | 7/2009 | Resnick et al. |
| 2009/0211593 | A1 | 8/2009 | Coppola et al. |
| 2010/0266651 | A1 | 10/2010 | Czech et al. |
| 2011/0039948 | A1 | 2/2011 | Lange et al. |
| 2011/0021955 | A1 | 9/2011 | Zhou et al. |
| 2011/0219552 | A1 | 9/2011 | Zhou et al. |
| 2012/0031420 | A1 | 2/2012 | Gormley et al. |
| 2012/0289649 | A1 | 11/2012 | Wagner et al. |
| 2013/0259820 | A1 | 10/2013 | Snyder et al. |
| 2014/0308224 | A1 | 10/2014 | Pilz et al. |
| 2015/0011449 | A1 | 1/2015 | Snyder et al. |
| 2015/0037270 | A1 | 2/2015 | Pressly et al. |
| 2015/0231069 | A1 | 8/2015 | Modi |
| 2015/0305469 | A1 | 10/2015 | Paul |
| 2015/0328102 | A1 | 11/2015 | Pressly et al. |
| 2016/0016397 | A1 | 1/2016 | Xie et al. |
| 2017/0291994 | A1 | 10/2017 | Wagner et al. |
| 2018/0344619 | A1 * | 12/2018 | Sun ............... A61Q 5/004 |

FOREIGN PATENT DOCUMENTS

| | | |
|---|---|---|
| CN | 104069033 A | 10/2014 |
| CN | 104692976 A | 9/2015 |
| CN | 104892976 A | 9/2015 |
| CN | 105062040 A | 11/2015 |
| CN | 105615536 A | 8/2016 |
| CN | 105815536 A | 8/2016 |
| CN | 106490571 A | 3/2017 |
| DE | 2904164 A1 | 8/1960 |
| DE | 1099169 B | 2/1961 |
| DE | 255346 A1 | 3/1988 |
| DE | 3800629 A1 | 7/1989 |
| DE | 4030160 A1 | 3/1992 |
| DE | 4139090 A1 | 6/1993 |
| DE | 4318539 A1 | 12/1994 |
| DE | 19609960 A1 | 9/1997 |
| DE | 19707970 A1 | 9/1998 |
| DE | 19859722 A1 | 6/2000 |
| DE | 19860239 A1 | 7/2000 |
| DE | 10036553 A1 | 9/2001 |
| DE | 10036522 A1 | 2/2002 |
| DE | 10036532 A1 | 2/2002 |
| DE | 10036533 A1 | 2/2002 |
| DE | 10038532 A1 | 2/2002 |
| DE | 10253152 A1 | 6/2004 |
| DE | 102004002206 A1 | 8/2005 |
| DE | 102004002208 A1 | 8/2005 |
| EP | 0660717 A1 | 5/1955 |
| EP | 0095676 A2 | 7/1983 |
| EP | 0282720 A2 | 9/1988 |
| EP | 0282720 B1 | 9/1988 |
| EP | 0431609 A2 | 6/1991 |
| EP | 0638128 A1 | 2/1995 |
| EP | 0780117 A1 | 6/1997 |
| EP | 0842656 A2 | 5/1998 |
| EP | 0938590 A1 | 9/1999 |
| EP | 1108765 A2 | 6/2001 |
| EP | 1892274 A2 | 2/2008 |
| EP | 2363387 | 9/2011 |
| EP | 2363387 A2 | 9/2011 |
| EP | 2576660 B1 | 4/2014 |
| FR | 2986704 A1 | 8/2013 |
| GB | 313892 | 6/1929 |
| GB | 320041 | 9/1929 |
| GB | 358491 | 10/1931 |
| GB | 388367 | 2/1933 |
| GB | 429915 | 6/1935 |
| GB | 474630 | 11/1937 |
| GB | 479905 | 2/1938 |
| GB | 497846 | 12/1938 |
| GB | 498818 | 1/1939 |
| GB | 541047 | 11/1941 |
| GB | 577998 | 6/1946 |
| GB | 577998 | 8/1946 |
| GB | 635708 | 4/1950 |
| GB | 643025 | 9/1950 |
| GB | 755321 | 8/1956 |
| GB | 766273 | 1/1957 |
| GB | 881714 | 11/1961 |
| GB | 924050 | 4/1963 |
| GB | 954086 | 4/1964 |
| GB | 981850 | 1/1965 |
| GB | 1087783 | 10/1967 |
| GB | 1427057 | 3/1976 |
| JP | 50135237 A | 4/1974 |
| JP | 56-18572 B2 | 4/1981 |
| JP | S57154101 A | 9/1982 |
| JP | H04353600 A | 12/1992 |
| JP | H07170904 A | 7/1995 |
| JP | H09227479 A | 2/1997 |
| JP | 2001114647 A | 4/2001 |
| JP | 2002-114849 A | 4/2002 |
| JP | 2002114849 | 4/2002 |
| JP | 2004210724 A | 7/2004 |
| JP | 2004269459 A | 9/2004 |
| JP | 2006075137 A | 3/2006 |
| JP | 2006-169323 A | 6/2006 |
| JP | 2006169323 | 6/2006 |
| JP | 2008011739 A | 1/2008 |
| JP | 2009273441 A | 11/2009 |
| JP | 2013051916 A | 3/2013 |
| JP | WO2014077385 A1 | 1/2017 |
| JP | 2017063619 A | 4/2017 |
| JP | 2017176006 A | 10/2017 |
| JP | 2018076278 A | 5/2018 |
| KR | 20040054557 A | 6/2004 |
| TW | 201143630 | 12/2011 |
| WO | 9218457 A1 | 10/1992 |
| WO | 9301791 A1 | 2/1993 |

(56) References Cited

FOREIGN PATENT DOCUMENTS

| | | |
|---|---|---|
| WO | 9410971 A1 | 5/1994 |
| WO | 9516664 A1 | 6/1995 |
| WO | 97/02844 A1 | 1/1997 |
| WO | 0196444 A1 | 12/2001 |
| WO | 021257 | 2/2002 |
| WO | 0210256 A1 | 2/2002 |
| WO | 0210257 A1 | 2/2002 |
| WO | 0210259 A1 | 2/2002 |
| WO | 0210257 A1 | 7/2002 |
| WO | 03044233 A1 | 5/2003 |
| WO | 2004059137 A2 | 8/2004 |
| WO | 2004069137 A2 | 8/2004 |
| WO | 2007/061793 A2 | 5/2007 |
| WO | 2009042083 A1 | 4/2009 |
| WO | 2009042083 A2 | 4/2009 |
| WO | 2010017651 A1 | 2/2010 |
| WO | 2012027369 A2 | 3/2012 |
| WO | 2012038334 A1 | 3/2012 |
| WO | 2012084826 A1 | 5/2012 |
| WO | 2012084826 | 6/2012 |
| WO | 2012084826 A1 | 6/2012 |
| WO | 2012143371 A1 | 10/2012 |
| WO | 2013017260 A1 | 2/2013 |
| WO | 2013017280 A1 | 2/2013 |
| WO | 2013117770 A2 | 8/2013 |
| WO | 2013117771 A2 | 8/2013 |
| WO | 2013148629 A1 | 10/2013 |
| WO | 2013148635 A1 | 10/2013 |
| WO | 2013148636 A1 | 10/2013 |
| WO | 2013148935 A1 | 10/2013 |
| WO | 2014072490 A1 | 5/2014 |
| WO | 2014077385 A1 | 5/2014 |
| WO | 2014072645 A1 | 6/2014 |
| WO | 2016046178 A1 | 3/2016 |
| WO | 2016048178 A1 | 3/2016 |
| WO | 2016/087795 A1 | 6/2016 |
| WO | 2017071663 A1 | 5/2017 |
| WO | 2017/155875 A1 | 9/2017 |

OTHER PUBLICATIONS

K. Khanbabaee, T. van Ree. Nat. Prod. Rep., 2001, 18, 641-649.

Pinteala M. et al.; Functional Polysiloxanes, 02. On the reaction of Hydroxypropyl- and Aminoalkyl-terminated Polydimethylsiloxanes with Cyclic Andhydrides, Polymer Bulletin, Springer, Heidelberg, DE, vol. 32, No. 2, Feb. 1, 1994, pp. 173-178 XP000425948.

International Search Report and Written Opinion dated Feb. 27, 2020.

International Search Report and Written Opinion dated Oct. 8, 2018.

Database WPI Week 200260 Thomson Scientific, London, GB, XP002784247.

Database WPI Week 200647 Thomson Scientific, London, GB, XP002784248.

Database Caplus [online] Chemical Abstracts Service, Ccumbus. Ohio, US, 1976, G.S. Gordin et al.; "Polysiloxanepropyl meleates and study of their surface activity", XP002764249.

Database WPi Week 201632 Thomson Scientific, London, GB, XP002784250.

R. Wagner et al: "Silicen-Modified-Carbohydrate-Surfactants,-III: Catonic and Anionic Compounds", Applied Organometallic Chemistry, vol. 11, No. 6, Jun. 1, 1997, ppg. 523-538, XP05501848.

Pinteala et al: "Functional Polysiloxanes 02, on the Reaction of Hydroxypropyl—and Aminoalkyl-Terminated Polydimethylsiloxanes With Cyclic Anydrides" Polymer Bulletin, SPinger Heidelberg. DE, vol. 32, No. 2, Feb. 1, 1994, pp. 173-178, XP000425948.

Database WPI Week 199749 Thomson Scientific, London, GB, XP002784251.

Database Caplus [online] Chemical Abstracts Service, Coumbus, Ohio, US, 1997, Tanabe Seiyaku Co. Ltd. "Hair waving preperations containing unsaturated carboxylic acid amides and esters", XP002784252.

Database Capias [online] Chemical Abstracts Service, Coumbus, Ohio, US, 1976, Tanabe Seiyaku Co. Ltd. "Hair waving preperations containing carboxylic acid esters or amides", XP002784253.

Database WPI Week 201837 Thomson Scientific, London, GB, XP002784254.

M.A Rogers, L. Langbein. S. Praetzel-Wunder. H. Winter, J Schweizer, J. Int Rev Cytol. 2006; 251:209.6.

H. Puchtler et al., "On the chemistry of formaldehyde fixation and its effects on immunohistochemical reactions", Histochemistry, 82(1985), pp. 201-204.

L. Ladriere et al., Molecular and Cellular Biochemistry (1999), 198 (1&2), 35-139.

L. Ladriere et al., "Can glyciol-1,2,3-tris(methylsuccinate) stimulate insulin release after oral administration?"; Medical Science Research (1999), 27(5), 303-304.

L. Ladriere et al., "Assessment of the Nutritional Value of Glycerol-1.2,3-tris (methylsuccinate in Fed and Starved Rats"; Molecular Genetics and Metabolism (1999), 67(3), 254-260.

T. Zhang et al, Abstracts 44th Central Regional Meeting of the American Chemical Society, Mount Pleasant, MI, May 15-17, 2013, CERM-6

N. R. Luman et at., Cover PictureChemistry—A European Journal (2003), 9(22), 5618-5626.

G. P. Andrews et al., "Branching Polyester Oligomers and Fractals"; ACS Symposium Series (2003), 834 SNMR Spectroscopy of Polymers in Solution and in the solid state), 216-227.

Pacifichem 2010: Abstract-The 2010 International: Honolulu: Chem. Eng. News Archieve, Dec. 15-20.

A. H. Fawcett et al. J. Pol Sci., Part A: Polymer Chemistry (1994), 32(5), 815-827.

K. Khanbabaee, T. van Rea, Nat. Prod. Rep., 2001, 18, 641-649.

Practical Modern Hair Science Trefor Evans and R. Randall Wichett, Alluredbooks, Carol Stream, Illinois, 2012.

https://en.wikipedia.org/wiki/Sugar_alcohol.

Sugarhara et al.; "Effect of inorganic and organic counterions on interfacial properties of oleic acid-based gemini surfactants"; Colloids and Surfaces A; 538: (2018) 73-78.

Bosch et al.: "Synethesis of Macrocyclic Dilactones through Lipases"; Department of Biological Organic Chemistry; (2005) 2611-2614.

Yang et al., "Hair Care Cosmetics": Cosmetic Science and Technolgy: Theoretical Principles and Applications; Beauty Hi-tech Innovation Co., Chapter 36 (2017).

Carbon Bonding (https://www.ck12.org/c/physical-science-carbon-bonding/lesson/Carbon-Bonding-MS-PS/) accesses May 17, 2019. pp. 1-5 (2019)

M. A. Rogers, L. Langbein, S. Praetzel-Wunder, H. Winter, J. Schweizer, J. Inl Rev Cytol. 2006; 251:209-6.

H. Puchtler, Histochemistry, 82(1985), pp. 201-204.

Z. Song. Z. Xiao, Linchan Huaxue Yu Gongye (1988), 8(3), 9-18.

T. Nagao, T Sayuri, T. Tatsuya, M. Yukari, S. Hideaki Journal of Oleo Science (2011), 60(9), 457-62.

Karamall Khanbabaee and Teunis van Ree, Nat. Prod. Rep., 2001, 18, 641-649 "Tannins: Classification and Definition".

http://ec.europa.eu/consumers/cosmetics/cosing/index.cfm?fuseaction=search.details_v2&id=92003.

M.A, Rogers et al., Human Hair Keratin-Associated Proteins (KAPs), International Review of Cytology, 2006, 251: 209-263.

K. Khanbabsee et al., "Tannins: Classification and Definition", Nat. Prod. Rep., 2001, 18: 641-649.

H. Puchtler et al., "On the chemistry of formaldehyde fixation and its effects on immunohistochemical reactions", Histochernistry, 1985 82: 201-204.

Dr. Frederic Pilz COSSMA (2010) vol. 7-8, p. 18.

http://ec.europa.eu/consumers/cosmetics/cosing/index.cfm?fuseaction=search.details_v2&id=92003 retrieved Nov. 17, 2017.

\* cited by examiner

USE OF POLYCARBOXYLIC ACID COMPOUNDS FOR THE TREATMENT OF FIBRIOUS AMINO ACID BASED SUBSTRATES, ESPECIALLY HAIR

FIELD OF THE INVENTION

This invention relates to the use of polycarboxylic acid compounds, aqueous compositions comprising the same, cosmetic compositions comprising the same, in particular, hair care compositions, for the treatment of hair, and a process for the treatment of fibrous amino acid based substrates, especially hair comprising the use of said cosmetic compositions.

BACKGROUND OF THE INVENTION

Hair generally can be straight, wavy, curly, kinky or twisted. A human hair includes three main morphological components, the cuticle (a thin, outer-most shell of several concentric layers), the cortex (the main body of the hair), and, in case of higher diameter hair, the medulla (a thin, central core). The cuticle and cortex provide the hair strand's mechanical properties, that is, its tendency to have a wave, curl, or kink. A straight hair strand can resemble a rod with a circular cross-section, a wavy hair strand can appear compressed into an oval cross-section, a curly strand can appear further compressed into an elongated ellipse cross-section, and a kinky hair strand cross-section can be flatter still.

The primary component of hair is the cross-linked, alpha-helix protein keratin. Keratins are intermediate filament proteins found specifically in epithelial cells, e.g. human skin and hair, wool, feathers, and nails. The α-helical type I and II keratin intermediate filament proteins (KIFs) with molecular weights around 45-60 kDa are embedded in an amorphous matrix of keratin-associated proteins (KAPs) with molecular weights between 20 to 30 kDa (M. A. Rogers, L. Langbein, S. Praetzel-Wunder, H. Winter, J. Schweizer, J. Int Rev Cytol. 2006; 251:209-6); both intra- and intermolecular disulfide bonds provided by cystines contribute to the cytoskeletal protein network maintaining the cellular scaffolding. In addition to the disulfide cross-links ionic bonding or salt bridges which pair various amino acids found in the hair proteins contribute to the hair strand's outward shape.

Traditionally, aldehyde based formulations for a permanent hair shaping and hair strengthening were developed. Most frequently formaldehyde is used for this so called Brazilian keratin shaping method (US 2012-0031420). The underlying principle is the crosslinking reaction between formaldehyde and keratin based amino and amido groups (H. Puchtler, Histochemistry, 82(1985), pp. 201-204) or between formaldehyde and —SH groups (US 2009-0211593).

Alternatively, U.S. Pat. No. 9,144,537 and US2015/0328102 describe salts of maleic acid with diamines or unsaturated amines for hair strengthening and color protection purposes.

Further, it is known in the art that hair can be treated with functionalized silicones which deliver one or more cosmetic benefits, such as conditioning, shine and UV protection as well as color retention. Typically, these silicones are physically deposited on the fiber surface (cuticle) and therefore responsible for the outward appearance of the hair. They can be removed partially or completely by repeated washing processes. While the deposited silicones considerably improve the surface properties of hair, i.e. smoothness and friction, they do not substantially impact the shape, the mechanical properties and the release properties of the hair.

Esters of diacetyltartaric acid with glycerol are known as food additives (WO2017071663, JP2017063619, CN105815536, TW2011143630, JPH07170904). These diacetyltartaric acid glycerol esters are also known in encapsulations (CN106490571) and in plastisizer formulations (CN104892976). Mixed esters of tartaric acid with fatty acids and glycerol are also known as food additives (JP2009273441, GB924050, GB1087783, GB881714). They were also proposed for other applications, i.e. resins (KR20040054557), finishes (JPH04353600, GB388367), alkyd formulations (GB954086, GB498818), lubricants (GB643025), photo (GB577998) and cosmetics (EP2363387). Tartaric acid glycerol ester were proposed i.e. for resins (GB320041, GB479905), for the modification of fibres (GB497846, GB541047) or as intermediate for emulsifiers (WO2010017651).

Si—O—C linked silicone-amino acid condensates for cosmetic applications are described in JP2001114647 and U.S. Pat. No. 5,854,319. DE10036522 and DE10036532 describe Si—C— linked amino acid modified silicones. WO2012084826 and U.S. Pat. No. 6,664,342 describe aspartic acid modified silicones. JP2004269459 describes aspartic acid modified silicone derivatives bearing a cyclic amino acid structure.

Alternative hair treatment methods are available, but these often involve the use of harsh and regulated substances.

Hence, there has been a need for efficient compounds for the treatment of hair which can be synthesized in a straight forward and cost efficient way, which are easy to formulate and easy to use, yielding long term stable formulations even in the presence of other performance ingredients and which are useful for strengthening of hair, for hair color retention, for hair color enhancement, hair color deepening, for hair color protection, for shaping of hair, i.e. the curling and straightening of hair, for hair conditioning, for hair smoothening or softening, for hair straightening, and for improving manageability of the hair, in particular for improving the combability of the hair. In particular, benefits regarding the retention of artificial hair colours without the usage of strongly irritating auxiliaries should be achieved.

The present inventors found that certain polyorganosiloxanes A) and/or certain organic compounds B) which carry specific functional groups are suitable to satisfy the above need. The present inventors found that said polyorganosiloxanes A) and/or organic compounds B) and aqueous compositions comprising the same can be synthesized in a straight forward and cost efficient way, are easy to formulate and to use, and are useful for the treatment of hair, in particular, for strengthening of hair, for hair color retention, for hair color enhancement, hair color deepening, for hair color protection, for shaping of hair, i.e. the curling and straightening of hair, for hair conditioning, for hair smoothening or softening, for hair straightening, and for improving manageability of the hair, in particular for improving the combability of the hair. In particular, the use of said polyorganosiloxanes A) and/or said organic compounds B) avoid the usage of strongly irritating auxiliaries.

SUMMARY OF THE INVENTION

In accordance with the present invention, the use of a polyorganosiloxane of formula (A) having an average number of 2 to 1000 siloxy units selected from the siloxy groups of the formulas:

(A)

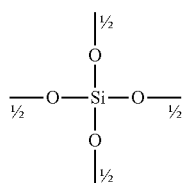

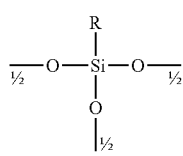

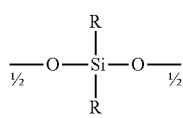

(Q)

(T)

(D)

(M)

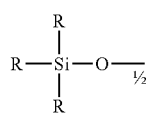

wherein
R is selected from $R^1$ and $R^F$, wherein
  $R^1$ is selected from organic groups bound to the silicon atoms by a carbon atom, and two groups $R^1$ may form a bridging group between two silicon atoms,
  $R^F$ is selected from organic groups different from $R^1$ and is bound to the silicon atoms by a carbon atom, and $R^F$ contains at least one functional group F selected from:

—O—C(O)—$R^3$—C(O)OH, and

—$NR^4$—C(O)—$R^3$—C(O)OH, and wherein the groups F bind to a carbon atom, wherein
$R^3$ is selected from a single bond or optionally substituted straight-chain, cyclic or branched, saturated, unsaturated or aromatic hydrocarbon radicals which have up to 100 carbon atoms, which optionally contain one or more groups selected from —O—, —NH—, —C(O)—, —C(S)—, tertiary amino groups

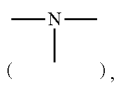

and quaternary ammonium groups

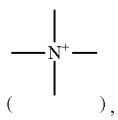

with the proviso that $R^3$ is not —CH═CH—, and
$R^4$ is selected from the group consisting of hydrogen, or optionally substituted straight-chain, cyclic or branched, saturated, unsaturated or aromatic hydrocarbon radicals which have up to 100 carbon atoms which optionally contain one or more groups selected from —O—, —NH—, —C(O)—, —C(S)—, tertiary amino groups

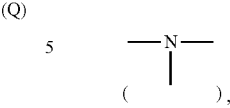

and quaternary ammonium groups

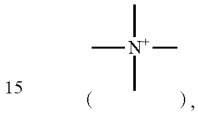

or a compound of formula (B):

$$R^2(—F)_{2-18} \quad (B)$$

wherein
$R^2$ is selected from divalent to octadecavalent, optionally substituted hydrocarbon radicals which have up to 100 carbon atoms, and may contain optionally one or more groups selected from —O—, —NH—, —C(O)—, —C(S)—, tertiary amino groups

and quaternary ammonium groups

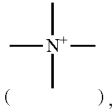

and F is as defined above,
or salts of said polyorganosiloxanes of formula (A) or said compound of formula (B),
in the color and shape treatment of hair, preferably in the color treatment of hair, is provided. In the present invention the color treatment of hair preferably comprises all kind of treatments involving hair coloring or hair color, e.g. applying hair color, deepening, enhancing or protecting hair color, retaining of hair color, etc. In the present invention "shape treatment of hairs" shall mean all kind of treatments that have an influence on the shape of hairs, in particular, hair strengthening, hair curling, hair straightening, generally improving the manageability of hairs, as outlined in more detail below.

Salts of the polyorganosiloxanes of formula (A) or the compounds of formula (B) of the invention may include for example an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium. The salts of compounds of the present invention can be prepared in particular by reacting the compounds of the present invention with the appropriate bases via a variety of known methods.

The groups F are of the formula selected from:

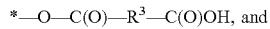

*—O—C(O)—R³—C(O)OH, and

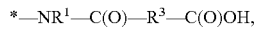

*—NR¹—C(O)—R³—C(O)OH, wherein the bond marked with the asterisk bind to a carbon atom of $R^2$.

The groups F can be also depicted as:

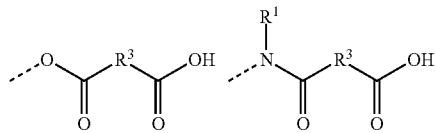

wherein the dotted lines bind to a carbon atom of $R^2$.

The preferred group F is *—O—C(O)—R³—C(O)OH.

In case $R^3$ has an asymmetric structure two isomers can be formed if the underlying dicarboxylic acids

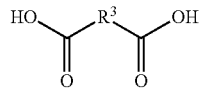

react with a compound providing the moiety $R^2$ of the compound (B) or the polyorganosiloxane moiety of the polyorganosiloxane (A) and such isomers are included in the scope of the inventions, even though they are not expressly mentioned.

In a preferred embodiment of the invention the optional substituents of the groups $R^2$, $R^3$ and $R^4$ are selected from the groups consisting of hydroxyl, amino and halogen, preferably hydroxyl and amino, and the number of the substituents may be up to 5, preferably 1 to 4.

In a preferred embodiment of the invention $R^4$ is selected from the group consisting of hydrogen, n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which optionally can be each substituted by hydroxyl and halogen, and which optionally can contain one or more ether groups (—O—), preferably hydrogen or n-, iso-, or tert.-$C_1$-$C_{22}$-alkyl. Most preferred $R^1$ is hydrogen.

In a preferred embodiment of the invention $R^2$ is selected from divalent to decavalent, more preferred divalent to hexavalent, even more preferred divalent, preferably aliphatic, hydrocarbon radicals which have 2 to 30 carbon atoms, more preferred 2 to 20 carbon atoms, even more preferred 2 to 15 carbon atoms and may contain optionally one or more groups selected from —O—, —NH—, —C(O)—, —C(S)—, and wherein $R^2$ may optionally be substituted by one or more hydroxyl groups.

In a preferred embodiment of the invention $R^2$ has a valency of 2 to 18, preferably 2 to 12, more preferably 2 to 10, and still more preferably 2 to 8, such as 2 to 6, specifically 2 or 3 or 4.

In a preferred embodiment of the invention $R^2$ is selected from the group consisting of:

divalent to octadecavalent, preferably divalent to hexavalent hydrocarbyl groups, more preferably divalent hydrocarbyl groups, derived from aliphatic polyols having more than three carbon atoms such as alkane di-, tri- and tetraols, e.g. 1,6 hexandiol, trimethylolpropane, and pentaerythritol, divalent to octadecavalent, preferably divalent to hexavalent hydrocarbyl groups, more preferably divalent hydrocarbyl groups, comprising at least one ether group, and optionally having one or more hydroxyl substituents, derived from polyalkyleneoxides, such as ethylene oxide-, propylene oxide- and/or butylene oxide-based polyethers, e.g. derived from polyethylene glycols, like diethylene glycol, triethylene glycol, tetraethylene glycol, and pentaethylene glycol etc., or derived from polypropylene glycols, like dipropylene glycol (e.g., derived from 2,2'-oxydi-1-propanol, 1,1'-oxydi-2-propanol, and 2-(2-hydroxypropoxy)-1-propanol), tripropylene glycol, tetrapropylene glycol, pentapropylene glycol, etc., derived from mixed ethylene oxide and butylene oxide based copoethers, derived from mixed propylene oxide and butylene oxide based copolyethers, and derived from mixed ethylene oxide and propylene oxide and butylene oxide based copolyethers, divalent to octadecavalent, preferably divalent to hexavalent hydrocarbyl groups, more preferably divalent hydrocarbyl groups, optionally comprising at least one ether group, and optionally having one or more hydroxyl substituents, derived from oligoglycerols, such as diglycerol, triglycerol, tetraglycerol, pentaglycerol, hexaglycerol, and the statistically distributed oligomeric condensation products of glycerol, such as divalent to octadecavalent, preferably divalent to hexavalent hydrocarbyl groups, more preferably divalent hydrocarbyl groups, derived from compounds comprising at least one glycidoxy group, such as diglycidyl ether, glycerol diglycidyl ether, and glycerol triglycidylether, divalent to octadecavalent, preferably divalent to hexavalent hydrocarbyl groups, more preferably divalent hydrocarbyl groups, comprising at least one ether group, and optionally having one or more hydroxyl substituents, derived from polyol alkylene oxide addition products, e.g. the addition products of ethylene oxide and/or propylene oxide to polyols such as ethylene glycol, 1,2 propylene glycol, glycerol, trimethylolpropane, pentaerythritol, sorbitol and sucrose, divalent to octadecavalent, preferably divalent to hexavalent hydrocarbyl groups, more preferably divalent hydrocarbyl groups, comprising at least one ether group, and optionally having one or more hydroxyl and/or amino substituents, derived from polyamine alkylene oxide addition products, e.g. the addition products of ethylene oxide and/or propylene oxide to ethylenediamine, diethylene triamine, or derived from alkylene oxide addition products of ethanol amine, divalent to octadecavalent, preferably divalent to hexavalent hydrocarbyl groups, more preferably divalent hydrocarbyl groups, comprising at least one ester group, and having one or more hydroxyl substituents, e.g. derived from polyesters, preferably derived from the condensation of di- to hexavalent carboxylic acids, e.g. maleic acid, succinic acid, adipic acid, sebacic acid, itaconic acid, tartaric acid, trimellitic acid with alkylene oxides, such as ethylene oxide, propylene oxide, butylene oxide, and compounds comprising at least one glycidoxy group, such as glycidol, diglycidyl ether, glycerol diglycidyl ether, glycerol triglycidyl ether, in particular the condensation products of succinic acid, maleic acid and tartaric acid to glycerol diglycidyl ether, further $R^2$ presents preferably polyalkylene oxy groups, preferably of the general formula:

—[CH$_2$CH$_2$O]$_{q1}$—[CH$_2$CH(CH$_3$)O]$_{r1}$—[CH$_2$CH(C$_2$H$_5$)O]$_{s1}$—{[CH$_2$CH$_2$]$_{q2}$—[CH$_2$CH(CH$_3$)]$_{r2}$—[CH$_2$CH(C$_2$H$_5$)]$_{s2}$}— with
q1=0 to 49, preferred 0 to 10, more preferred 1 to 10, even more preferred 1 to 5,
r1=0 to 32, preferred 0 to 10, more preferred 1 to 10, even more preferred 1 to 5,
s1=0 to 24, preferred 0 to 10, more preferred 1 to 10, even more preferred 1 to 5,
q2=0 or 1,
r2=0 or 1,
s2=0 or 1, and $\Sigma(q2+r2+s2)=1$, with the proviso that the sum of the carbon atoms in such polyalkylene oxide groups is 2 to 100, preferred 2 to 50, more preferred 2 to 30, even more preferred 2 to 20, specific 2 to 15,
divalent hydrocarbyl groups, derived from oligoglycerols of the general formula:

—[CH$_2$CH(R$^7$)CH$_2$O]$_{t1}$—[CH$_2$CH(R$^7$)CH$_2$)]$_{t2}$— with
t1=0 to 32, preferred 0 to 10, more preferred 1 to 10, even more preferred 1 to 5, specifically 1 and 2,
t2=1,
R$^7$=OH or F, wherein F is as defined above, preferably —O—C(O)—R$^3$—C(O)OH,
with the proviso that the sum of the carbon atoms is 2 to 100, preferred 2 to 50, more preferred 2 to 30, even more preferred 2 to 20, specific 2 to 15, and
divalent hydrocarbyl groups, comprising at least one ester group of the general formulae:

—[CH$_2$CH$_2$O]$_{q1}$—R$^8$—[CH$_2$CH$_2$O]$_{q1}$—[CH$_2$CH$_2$]$_{q2}$— with q1 can be the same or different and are as defined above and q2=1 and

—[CH$_2$CH(R$^7$)CH$_2$O]$_{t1}$—R$^8$—[CH$_2$CH(R$^7$)CH$_2$O]$_{t1}$—[CH$_2$CH(R$^7$)CH$_2$)]$_{t2}$— with t1, t2 and R$^7$ as defined above and
R$^8$ being selected from —C(O)C(O)O—, —C(O)(CH$_2$)$_{1-8}$C(O)O—, such as being derived from succinic acid, adipic acid, sebacic acid, or —C(O)(C$_6$H$_4$)C(O)O—, i.e. derived from phthalic and terephthalic acid, —C(O)CH=CHC(O)O—, —C(O)C(=CH$_2$)—CH$_2$C(O)O—, —C(O)CH(OH)CH(OH)C(O)O—,
with the proviso that the sum of the carbon atoms in R$^2$ is 2 to 100, preferred 2 to 50, more preferred 2 to 30, even more preferred 2 to 20, specifically 2 to 15.

In a preferred embodiment of the invention R$^2$ contains one or more groups —O—, such as one to five. These groups —O— are preferably ether groups, but can also form an ester group together with a carbonyl group. Preferably the groups R$^2$ and is substituted by one or more hydroxyl groups.

In a preferred embodiment of the invention the compound according to the invention has the formula:

wherein R$^5$ is selected from the group consisting of hydroxy or F, wherein F is as defined above, with the proviso that at least two of R$^5$ are F.

In a preferred embodiment of the invention the compound according to the invention has the formula:

wherein one of R$^9$ is hydroxy and one of R$^9$ is a group of the formula and wherein F is as defined above and the dotted line is the bond to the carbon atom.

In a preferred embodiment of the invention the compound according to the invention is a mixture of the following two isomers:

wherein F is as defined above.

Examples for precursors for glycerol moieties containing compounds according to the invention are the glycidyl functional Denacol types EX-313, EX-314, EX-421, EX 512, EX 521 (Nagase). Examples for precursors for trimethylolpropane, pentaerythrol and neopentyl glycol moieties containing compounds according to the invention are the glycidyl functional Denacol types EX-321, EX-411 and EX-211 (Nagase).

In a preferred embodiment of the invention the compound according to the invention has the formula:

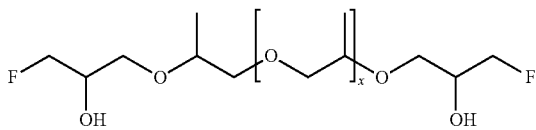

wherein x is from 1 to 10, preferably 1 to 5, and F is as defined above.

Examples for precursors for propylene glycol moieties containing compounds according to the invention are the glycidyl functional Denacol types EX-920, EX-921 (Nagase).

Examples for precursors for ethylene glycol moieties containing compounds according to the invention are the glycidyl functional Denacol types EX-821, EX-830, EX-832, EX-841, EX-850, EX-851, EX-861 (Nagase).

In a preferred embodiment of the invention $R^3$ is selected from the group consisting of a single bond and straight-chain, cyclic or branched, saturated, unsaturated or aromatic hydrocarbon radicals which have up to 18, preferably up to 12, more preferably up to 10 carbon atoms, and which optionally contain one or more groups selected from —O—, —NH—, —C(O)—, and wherein $R^3$ is optionally substituted by one or more groups selected from hydroxyl groups, amino groups, and carboxy groups.

In a preferred embodiment of the invention $R^3$ is derived from a dicarboxylic acid. Here and in the context of the present invention "derived from" shall mean in particular, residues that are formally formed from compounds by reacting those compounds to arrive at the compounds of the invention. For example, considering the embodiment where $R^3$ is derived from a dicarboxylic acid, in such case $R^3$ derived from a dicarboxylic acid would result e.g. from the reaction of a polyol or a polyepoxide or a polyamine of formula:

wherein A is OH and/or an epoxy group and/or an amino group, preferably OH and/or an epoxy group, preferably an epoxy group of the formula:

and wherein c=2-18, preferably c=2 to 10, more preferably c=2 to 8, more preferably c=2 to 4, with a dicarboxylic acid

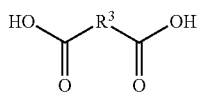

to form e.g.

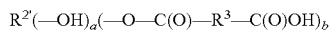

or

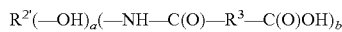

with b≥2 and a+b=2 to 18, preferably b=2 to 6, more preferably b=2 to 4, more preferably b=2, and a+b=preferably 2 to 8, more preferably a+b=2 to 6, and wherein $R^{2'}$ are each moieties that contributes to the formation of $R^2$.

In a preferred embodiment of the invention $R^3$ is derived from a dicarboxylic acid of the formula:

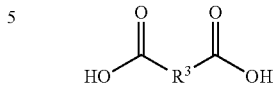

wherein $R^3$ is as defined above, such as optionally substituted aliphatic, saturated or unsaturated or aromatic dicarboxylic acids, such as oxalic acid (ethanedioic acid), malonic acid (propanedioic acid), succinic acid (butanedioic acid), glutaric acid (pentanedioic acid), adipic acid (hexanedioic acid), pimelic acid (heptanedioic acid), suberic acid (octanedioic acid), azelaic acid (nonanedioic acid), sebacic acid (decanedioic acid), undecanedioic acid, dodecanedioic acid, brassylic acid (tridecanedioic acid), thapsic acid (hexadecanedioic acid), glutaconic acid (pent-2-enedioic acid), citraconic acid ((2Z)-2-methylbut-2-enedioic acid), mesaconic acid ((2E)-2-methyl-2-butenedioic acid), itaconic acid (2-methylidenebutanedioic acid), tartronic acid (2-hydroxypropanedioic acid), mesoxalic acid (oxopropanedioic acid), malic acid (hydroxybutanedioic acid), tartaric acid (2,3-dihydroxybutanedioic acid), oxaloacetic acid (oxobutanedioic acid), aspartic acid (2-aminobutanedioic acid), α-hydroxy glutaric acid (2-hydroxypentanedioic acid), arabinaric acid (2,3,4-trihydroxypentanedioic acid), acetonedicarboxylic acid (3-oxopentanedioic acid), α-ketoglutaric acid (2-oxopentanedioic acid), glutamic acid (2-aminopentanedioic acid), diaminopimelic acid ((2R,6S)-2,6-diaminoheptanedioic acid), saccharic acid ((2S,3S,4S,5R)-2,3,4,5-tetrahydroxyhexanedioic acid), phthalic acid (benzene-1,2-dicarboxylic acid), isophthalic acid (benzene-1,3-dicarboxylic acid), terepthtalic acid ((benzene-1,3-dicarboxylic acid)), diphenic acid (2-(2-carboxyphenyl)benzoic acid), 2,6-naphthalenedicarboxylic acid, norbornene dicarboxylic acid, norbornane dicarboxylic acid, and trimellitic acid, or $R^3$ is derived from an aliphatic or aromatic tricarboxylic acid, wherein $R^3$ is substituted with carboxyl group (COOH), such as citric acid (2-hydroxypropane-1,2,3-tricarboxylic acid), isocitric acid (1-hydroxypropane-1,2,3-tricarboxylic acid), aconitic acid ((cis or trans prop-1-ene-1,2,3-tricarboxylic acid), propane-1,2,3-tricarboxylic acid; trimesic acid (benzene-1,3,5-tricarboxylic acid). Preferred dicarboxylic acids include: succinic acid, adipic acid, itaconic acid, tartaric acid, the reaction products of carboxylic acid anhydrides, such as maleic anhydride and succinic anhydride, with amino acids and amino acid derivatives, such as β-alanine and asparagine, i.e. N-acetyl aspartic acid, N-maleoyl-β-alanine ((E)-4-(2-carboxyethylamino)-4-oxo-but-2-enoic acid), N-maleoyl-asparagine (4-amino-2-[[(E)-4-hydroxy-4-oxo-but-2-enoyl]amino]-4-oxo-butanoic acid), etc. As mentioned above asymmetric dicarboxylic acids may lead to the formation of isomers, which are all included in the scope of the present invention.

Most preferred for hair color deepening are succinic acid and tartaric acid. Most preferred for hair color retention (lower color loss value) are succinic acid, tartaric acid, N-acetyl aspartic acid and N-maleoyl-β-alanine ((E)-4-(2-carboxyethylamino)-4-oxo-but-2-enoic acid.

Also anhydrides of such dicarboxylic acids such as succinic acid anhydride, itaconic acid anhydride, etc. can be used to react e.g. with hydroxyl and/or amino functional compounds of the formula $R^{2'}(-A)_c$ as defined before.

In a preferred embodiment of the invention F is selected from the group consisting of the formulas:

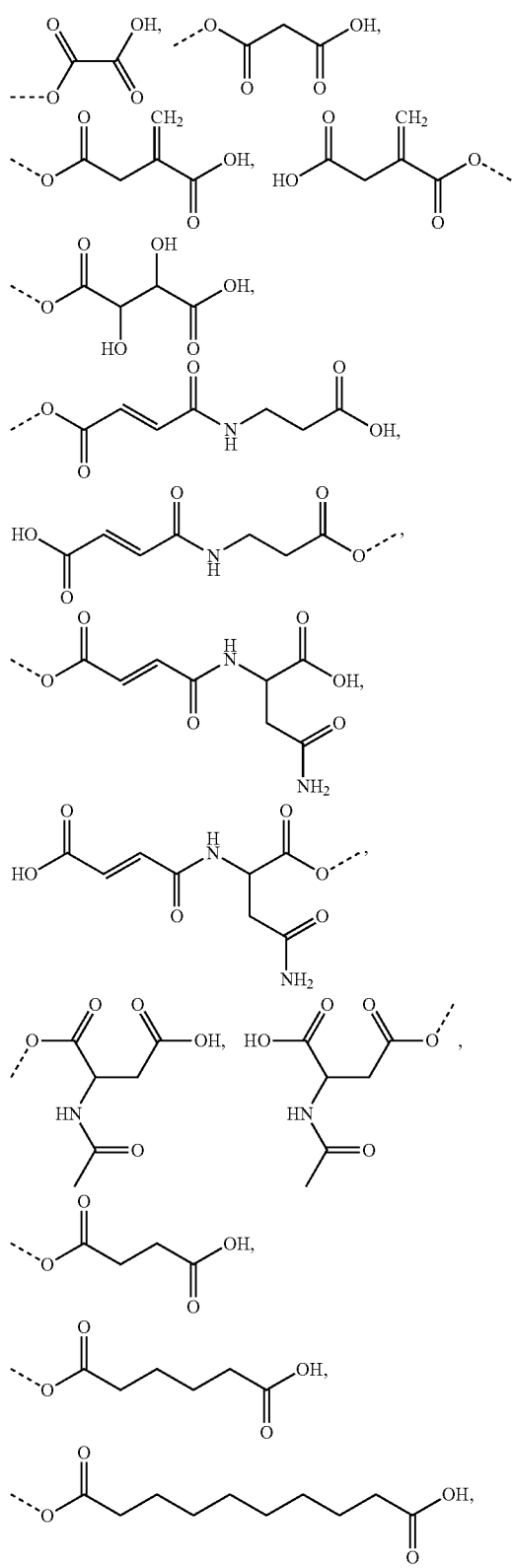

wherein the dotted line in the above formulae represents the bond to the oxygen atom, and wherein there are at least two groups F.

In a further preferred embodiment of the invention $R^2$ is not derived from a carbohydrate (saccharide), such as monosaccharides, disaccharides, oligosaccharides, and polysaccharides, or a sugar alcohol. A carbohydrate or saccharide is a biomolecule consisting of carbon (C), hydrogen (H) and oxygen (O) atoms, usually with a hydrogen-oxygen atom ratio of 2:1 (as in water) and thus with the empirical formula $C_m(H_2O)_n$ (where m may be different from n). They also include deoxyribose, and structurally include in particular aldoses and ketoses, residues derived from which are thus preferably excluded from $R^2$. Sugar alcohols (also called polyhydric alcohols, polyalcohols, alditols or glycitols) are organic compounds, typically derived from sugars, that comprise a class of polyols, and commonly include e.g. ethylene glycol, glycerol, erythritol, threitol, arabitol, xylitol, ribitol, mannitol, sorbitol, galactitol, fucitol, iditol, inositol etc. (see e.g. https://en.wikipedia.org/wiki/Sugar_alcohol). In particular, $R^2$ derived from ethylene glycol and glycerol are preferably excluded.

A further embodiment of the invention relates to a process for the manufacture of the polyorganosiloxane of formula (A) or the (non-polyorganosiloxane) compound of formula (B) according to the invention, which process is selected from the group consisting of the following processes:

(A) Reacting at least one polyorganosiloxane or at least one (non-polyorganosiloxane) compound each having at least two epoxy groups, said compound optionally may have one or more hydroxyl groups, with at least one di- or tricarboxylic acid compound to form the polyorganosiloxane of formula (A) or the compound of formula (B) according to the invention, (B) Reacting at least one polyorganosiloxane or at least one (non-polyorganosiloxane) compound each having at least one epoxy group, which compound optionally may have one or more hydroxyl groups, with at least one di- or tricarboxylic acid compound, and subsequently subjecting the reaction product to the reaction with at least one acid anhydride, compound to form the polyorganosiloxane of formula (A) or the compound of formula (B) according to the invention, (C) Reacting at least one at least one polyorganosiloxane or at least one (non-polyorganosiloxane) compound each having at least two hydroxy groups with at least one acid anhydride, compound to form the polyorganosiloxane of formula (A) or the compound of formula (B) according to the invention, (D) Reacting at least one polyorganosiloxane or at least one (non-polyorganosiloxane) compound each having at least two amino groups with at least one acid anhydride compound to form the polyorganosiloxane of formula (A) or the compound of formula (B) according to the invention.

In a preferred embodiment of the invention the polyorganosiloxane (A) comprises at least two groups $R^F$. $R^F$ is selected from organic groups different from $R^1$ and is bound to the silicon atoms by a carbon atom, and $R^F$ contains at least one functional group F as defined above. The groups $R^F$ comprise in particular organic groups $R^{1'}$ which are substituted with at least one, preferably one group F as defined above, that is, $R^F$ is preferably a group $R^{1'}$—F, wherein $R^{1'}$ is $R^1$ wherein formally one hydrogen atom at a carbon atom of $R^1$ is removed (and replaced by F). Accordingly with respect to the definition of $R^{1'}$ it can be also referred to the definitions of $R^1$ below. Preferably $R^{1'}$ is selected from optionally substituted straight-chain, cyclic or branched, saturated, unsaturated or aromatic hydrocarbon radicals which have up to 100 carbon atoms, which optionally contain one or more groups selected from —O—, —NH—, —C(O)—, —C(S)—, tertiary amino groups

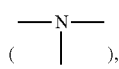

and quaternary ammonium groups

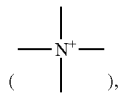

wherein said optional substituents are preferably selected from hydroxy, and said hydrocarbon radicals are bound to the silicon atoms by a carbon atom.

Preferably $R^{1'}$ is selected from a divalent hydrocarbon radical which has up to 30 carbon atoms, preferred 1 to 12, more preferred 1 to 8, even more preferred 3 to 8, specifically 3 to 6 carbon atoms, which optionally contains one or more groups selected from —O—, —NH—, —C(O)—, and wherein $R^{1'}$ optionally is substituted by one or more hydroxyl groups and $R^{1'}$ is bound to silicon by a carbon atom.

In a preferred embodiment the group $R^{1'}$ results from the reaction of epoxy-modified silicones with dicarboxylic acids of the formula:

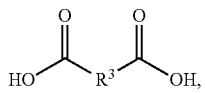

wherein $R^3$ is as defined above, such as tartaric acid and N-acetyl aspartic acid. In the most preferred embodiment $R^{1'}$ is derived from the reaction of glycidoxypropyl-terminated polysiloxanes (derived from the reaction of SiH polysiloxanes with allylglydiyl ether) schematically shown by the formula:

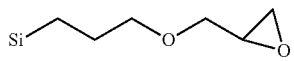

with dicarboxylic acids of the formula:

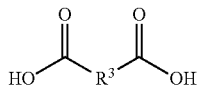

to form:

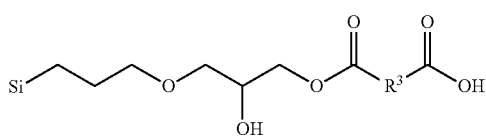

wherein $R^{1'}$ is a group of the formula:

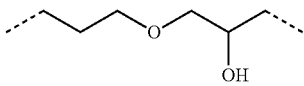

wherein the dotted lines represent the bonds the silicon atom and the oxygen atom of the group —O—C(O)—$R^3$—C(O)OH.

In a preferred embodiment in the polyorganosiloxane (A) the molar portion of the siloxanyl units which contain the group $R^F$ to all siloxanyl units of the polyorganosiloxane (A) is 3.33 to 100 mol %, more preferred 5 to 100 mol %, even more preferred 5 to 50 mol %, most preferred 10 to 50 mol %.

In another preferred embodiment of the invention in the polyorganosiloxane (A) the molar portion of branching T and Q moieties is 0 to 50%, preferred 0 to 20%, more preferred 0 to 10%, specifically 0 to 5%, more specifically 0% based on the number ok all siloxy units.

The average number of siloxy units in the polysiloxanes (A) is 2 to 300, preferably 2 to 30, even more preferred 2 to 20, even more preferred 2 to 15, specifically 2 to 12, more specifically 2 to 10, even more specifically 2 to 8. The average number on siloxy units can be determined i.e. by GPC (Gel Permeation Chromatography) using a system calibration versus polystyrene standards.

It is within the scope of the invention to use mixtures of different polysiloxanes A) according to the invention. Mixtures of polysiloxanes A) may yield bi-, tri- and higher modal molecular weight distributions, differing in the siloxane chain length. Mixtures of two polysiloxanes A) having a bimodal distribution are preferred. One preferred embodiment of the invention is a mixture comprising short chained siloxanes bearing on average 2 to 15 siloxy units and longer chained siloxanes bearing on average 16 to 30 siloxy units. Such mixtures have the advantage that depending on the size of the molecules different locations within the hair structure can be modified with silicone polymers.

The organic groups R are selected from $R^1$ and $R^F$ as defined above. Preferably the organic groups $R^1$ are independently selected from the group consisting of straight-chain, cyclic or branched, saturated, unsaturated or aromatic hydrocarbon radicals which have up to 100 carbon atoms which optionally contain one or more groups selected from —O—, —NH—, —C(O)—, —C(S)—, tertiary amino groups

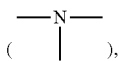

and quaternary ammonium groups

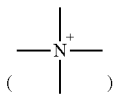

and which are optionally substituted by one more groups selected from the group consisting of hydroxyl, halogen (like chlorine, fluorine),
a polyether radical with up to 60 carbon atoms, or two radicals $R^1$ from different siloxy moieties form a straight-chain, cyclic or branched, saturated, unsaturated or aromatic alkandiyl hydrocarbon radical which has 2 to 20 carbon atoms between two silicon atoms, which are optionally substituted by one or more hydroxyl groups or halogen atoms, and are linked to silicon by a carbon atom, more preferably $R^1$ is selected from the group consisting of n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which optionally can be each substituted by hydroxyl and halogen, and which optionally can contain one or more ether groups (—O—), still more preferably, the radicals $R^1$ include: n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which can be substituted by one or more, preferred up to five, groups selected from hydroxyl and halogen, preferred fluorine, and can contain one or more ether groups, i.e. $H_3C$—, $CH_3CH_2$—, $CH_3CH_2CH_2$—, $(CH_3)_2CH$—, $C_8H_{17}$— and $C_{10}H_{21}$—, $H_2C$=$CH$—$O$—$(CH_2)_{1-6}$, cycloaliphatic radicals, i.e. cyclohexylethyl, limonyl, norbonenyl, phenyl, tolyl, xylyl, benzyl and 2-phenylethyl, halogen($C_1$-$C_{10}$)alkyl, i.e. $C_fF_{fn+1}CH_2CH_2$— wherein f is 1 to 8, i.e. $CF_3CH_2CH_2$—, $C_4F_9CH_2CH_2$—, $C_6F_{13}CH_2CH_2$—, $C_2F_5$—$O(CF_2$—$CF_2$—$O)_{1-10}$—$CF_2$—, $F[CF(CF_3)$—$CF_2$—$O]_{1-5}$—$(CF_2)_{0-2}$—, $C_3F_7$—$OCF(CF_3)$— and $C_3F_7$—$OCF(CF_3)$—$CF_2$—$OCF(CF_3)$— (in this context F denotes a fluorine atom), and still more preferred $R^1$ is selected from the group consisting of methyl, vinyl, phenyl, 3,3,3-trifluoropropyl, most preferred $R^1$ is methyl.

In a preferred embodiment the polysiloxane (A) invention contains at least two radicals of the formula $M^F$ and/or $D^F$:

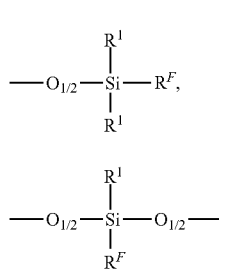

wherein $R^1$ and $R^F$ are as defined above.

In a further preferred embodiment the polysiloxane (A) is selected from the formulas:

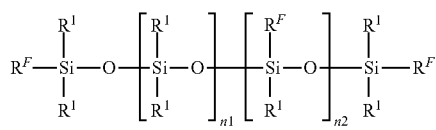

wherein $R^1$ and $R^F$ are as defined above, and n1+n2 is 0 to 28, preferred 0 to 20, more preferred 0 to 15, and n2 is preferably 0,

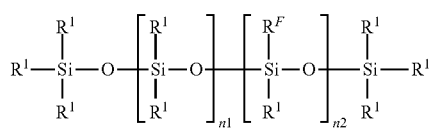

wherein $R^1$ and $R^F$ are as defined above, n1+n2 is 2 to 28, preferred 2 to 20, more preferred 2 to 15, even more preferred 5 to 15, with n2≥2, preferred 2 to 28, more preferred 2 to 10, even more preferred 2 to 5, and

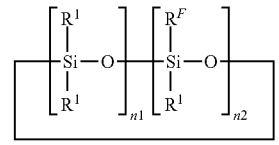

wherein $R^1$ and $R^F$ are as defined above, n1+n2 is 3 to 7 with n2≥2, preferred n1+n2 is 2 to 7, more preferred 2 to 5, even more preferred 3 to 5.

In a preferred embodiment the polysiloxanes (A) according to the invention have number-average molecular weights Mw<2000 g/mol, preferred <1500 g/mol, more preferred <1000 g/mol, as determined by GPC using polystyrene as standard.

In a preferred embodiment of the invention mixtures of more than one type of polysiloxanes A) according to the invention are used.

In accordance with the present invention it is possible that the polyorganosiloxane (A) in addition to the functionalized groups $R^F$ as defined above may carry further functional organic groups $R^{FA}$ which are selected from organic groups different from $R^1$ and $R^F$ and which contain at least one functional group FA selected from the group consisting of:

an optionally substituted azetidine or azetidinium group,
a methylol group,
a mono-, di-, trihydroxy-substituted aromatic group,
a thio ester and
a thio ether group,
alkoxy silyl group,
amino group,
ammonium group,
phosphonium group,
epoxy group,
carbonate group,
urethane group,
isocyanate group, including blocked iscocyanate group,
urea group,
amido group,
aldehyde group,
acetal or half acetal group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
mercapto group,
saccharide group, and
polyether group with up to 60 carbon atoms.

Such functional groups FA may also replace the functional group F in the polyorganosiloxane (A) and the organic compound (B) as long as there remain preferably at least two groups F in the polyorganosiloxane (A) or the organic compound (B) of formula $R^2$(—F)$_{2-18}$ as defined above. A particular preferred combination of the functional groups F and FA is a combination of F as defined above and a mono-, di-, trihydroxy-substituted aromatic group, such as with $R^{FA}$ having the structure:

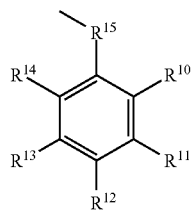

wherein
$R^{15}$ is selected independently from $R^{1'}$ as defined above, with the additional possibility that $R^{1'}$ is substituted by nitrogen containing groups, such as —$NH_2$, —$N(R^4)_2$, wherein $R^4$ is as defined above,
$R^{10}$, $R^{11}$, $R^{12}$, $R^{13}$, $R^{14}$ are the same or different from each other and are selected from hydroxyl, hydrogen and $R^1$, as defined above, preferably hydrogen and hydroxyl, with the proviso that 2 to 3 groups $R^{10}$ to $R^{14}$ are hydroxyl (—OH).

A particularly preferred group $R^{FA}$ is

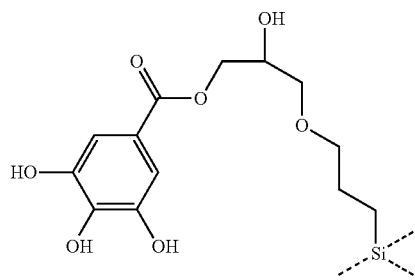

(dotted lines are free valencies of the silicon atom).

In another preferred embodiment of the present invention the polysiloxanes (A) according to the invention are combined with other functional polysiloxanes having preferably functional groups selected from amino, quaternary ammonium, and quaternary phosphonium groups alone or optionally in combination with anionic polysiloxane compounds having functional group selected from carboxylic acid/carboxylate, sulphonic acid/sulphonate, sulfuric acid half ester/sulphate, phosphoric acid ester/phosphate, phosphonic acid ester/phosphonate, phosphorous acid ester/phosphite, and xanthogenate/xanthogenate ester. Examples for the above mentioned compounds are described in WO 2012/143371. It is also preferred to combine the polysiloxanes according to the invention with betaine functional polysiloxanes. Examples for these compounds are described in WO 2012/143371. It is further preferred to combine the polysiloxanes according to the invention with di- and polycationic compounds of the ABA or block copolymer type. Examples for these compounds are described in WO 02/10257, WO 02/10259 and DE 10036553.

Another preferred embodiment of the present invention relates to the use of aqueous compositions comprising at least one of the polyorganosiloxane (A) and/or at least one of the compound (B) as defined above in the color and shape treatment of hair, preferably in the color treatment of hair, and preferably the aqueous compositions comprise at least one of the polyorganosiloxane (A) or at least one of the compound (B). Preferably the aqueous compositions comprise from 0.05 to 30 wt-%, preferably 0.1 to 20 wt-%, preferably 0.5 to 15 wt-%, more preferably 1 to 10 wt-% of at least one of the polyorganosiloxane (A) and/or at least one of the compound (B) based on the total weight of the aqueous compositions.

Optionally, the aqueous compositions comprise at least one metal salt, in particular as described below and optional at least one surfactant. Further, optionally the aqueous composition comprises at least one surfactant, which is preferably selected from cationic, nonionic, betaine and anionic surfactants, preferably having a HLB value ranging from 1 to 20, preferred 7 to 20, more preferred 8 to 20. More preferably the optional surfactant is selected from hydrocarbon based or silicone based emulsifiers each being different from polyorganosiloxane (A) and compound (B). The amount of the optional surfactant in the aqueous compositions according to the invention is preferably from about 0.05% to about 15%, more preferably from about 0.05% to about 5%, still more preferably from about 0.1% to about 5%, specifically from 0.1 to 3% by weight of the aqueous composition.

The weight ratio of the optional surfactant to the polyorganosiloxanes A) preferably is at least 0.06, preferred 0.06 to 5, more preferred 0.06 to 3, even more preferred 0.1 to 3, specifically 0.1 to 1. Depending on the chemical nature of the continuous and discontinuous phase emulsifiers having a HLB value <7 (W/O emulsion type) or >7 (O/W emulsion type) are preferably selected.

In a preferred embodiment of the invention the hair treatment composition provided is a W/O emulsion (preferably a water-in-oil-emulsion (W/O-emulsion)).

In another preferred embodiment of the invention the hair treatment composition provided is an O/W formulation (preferably an oil-in-water-emulsion (O/W-emulsion)).

Preferred examples for hydrocarbon based emulsifiers are cationic, nonionic, betaine and anionic emulsifiers.

Preferred examples for cationic emulsifiers are quaternary ammonium groups or amino groups containing linear or branched C8 to C50, preferred C8 to 40, more preferred C8 to C30 alkyl, fatty alcohol and fatty acid based emulsifiers, i.e. fatty acid based ester quats containing one or two fatty acid moieties, fatty amines and ethoxylated/propoxylated fatty amines.

Preferably, the cationic surfactant is a mono-long alkyl-tri short alkyl quaternized ammonium salt or di-long alkyl-di short alkyl quaternized ammonium salt wherein one or two alkyl substituents are selected from an aliphatic group of from about 8 to about 30 carbon atoms or an aromatic, alkoxy, polyoxyalkylene, alkylamido, hydroxyalkyl, aryl or alkylaryl group having up to about 30 carbon atoms; the other alkyl groups are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and the counter ion is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 8 carbons, or higher, can be saturated or unsaturated.

Preferably, one alkyl group is selected from an alkyl group of from about 8 to about 30 carbon atoms, more preferably from about 14 to about 26 carbon atoms, still more preferably from about 14 to 22 carbon atoms; the other alkyl groups are independently selected from the group consisting of —$CH_3$, —$C_2H_5$, —$C_2H_4OH$, —$CH_2C_6H_5$, and mixtures thereof; and the counter ion is selected from the group consisting of $Cl^-$, $Br^-$, $CH_3OSO_3^-$, and mixtures thereof. It is believed that such mono-long alkyl quaternized ammonium salts can provide, in addition to their emulsification capability, improved slippery and slick feel on wet hair, compared to multi-long alkyl quaternized ammonium salts. It is also believed that mono-long alkyl quaternized ammonium salts can provide improved hydrophobicity and smooth feel on dry hair, compared to amine or amine salt cationic surfactants.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

Preferred cationic surfactants are saturated or unsaturated fatty acid based mono-ester and di-ester quats (quats=quaternary ammonium cation comprising compound) having 10 to 18 carbon atoms in the alkyl chain. Commercially available examples are Arquad PC SV-60 PG and Armocare VGH70 (Akzo Nobel).

Details on cationic surfactants are disclosed in US2013/259820.

The aqueous compositions of the present invention preferably comprise the optional cationic surfactant in amount of from about 0.05% to about 15%, preferably from about 0.05% to about 5%, still more preferably from about 0.1% to about 5%, specifically from 0.1 to 3% by weight of the composition.

Preferred examples for nonionic emulsifiers are ethylene oxide (EO), propylene oxide (PO) and butylene oxide (BO) containing linear or branched C8 to C50, preferred C8 to 40, more preferred C8 to C24 fatty alcohol and fatty acid based emulsifiers as well as saccharide based emulsifiers, i.e. alkyl glycosides, alkoxylated fatty acid sorbitane esters and fatty acid glucamides. Another variety of preferred nonionic surfactants are the semi-polar amine oxides, phosphine oxides, and sulfoxides.

Preferred nonionic surfactants are saturated or unsaturated natural alcohol based ethoxylates having 10 to 18 carbon atoms in the alkyl chain and 5 to 80 EO units. Commercially available examples are the Genapol C, LA. V, O and T types (Clariant).

Preferred nonionic surfactants are linear or branched oxo alcohol based ethoxylates having 11 to 17 carbon atoms in the alkyl chain and 5 to 100 EO units. Commercially available examples are the Genapol UD, OA, OX, X, LCN types (Clariant).

Preferred nonionic surfactants are saturated or unsaturated alcohol based block ethoxylates-propoxylates having 10 to 18 carbon atoms in the alkyl chain and 2 to 20 EO units. Commercially available examples are the Genapol EP types (Clariant).

Preferred nonionic surfactants are ethoxylate-propoxylate block copolymers containing 5 to 70% wt % EO units. Commercially available examples are the Genapol PF and PH types (Clariant).

Preferred nonionic surfactants are saturated or unsaturated fatty acid based ethoxylates having 10 to 18 carbon atoms in the alkyl chain and 5 to 100 EO units. Commercially available examples are the Genagen O and S types (Clariant).

Preferred nonionic surfactants are saturated or unsaturated fatty acid based castor oil ethoxylates having 10 to 18 carbon atoms in the alkyl chains and 5 to 80 EO units. Commercially available examples are the Emulsogen HCO and EL types (Clariant).

Preferred nonionic surfactants are saturated or unsaturated fatty acid derivatized oligoglycerines. Preferred examples are fatty acid derivatized di-, tri, or tetraglycerines, i.e. mono- or diesters of diglycerine having 10 to 18 carbon atoms in the alkyl chain and optionally 5 to 100 EO units. Commercially available examples are the Hostacerine types (Clariant).

Preferred nonionic surfactants are saturated or unsaturated fatty acid sorbitane ester based ethoxylates having 10 to 18 carbon atoms in the alkyl chain and 5 to 50 EO units attached to the sorbitane ring. A commercially available example is Emulsogen 4156 (Clariant).

Preferred nonionic surfactants are saturated or unsaturated alcohol based glycosides having 8 to 18 carbon atoms in the alkyl chain and 1 to 10 glycosyl units. Commercially available examples are Plantacare 818 up and 1200 up (BASF).

Preferred nonionic surfactants are saturated or unsaturated fatty acid based glucamides, preferred fatty acid N-methylglucamides, having 8 to 18 carbon atoms in the alkyl chain. A commercially available example is the MEGA-10 type (Avanti).

Preferred nonionic surfactants are saturated or unsaturated fatty acid based alkanolamides, preferred fatty acid based ethanolamides, having 8 to 18 carbon atoms in the alkyl chain. Commercially available examples are the Aminon C types (Kao).

Preferred nonionic surfactants are the fatty amine or fatty acid amide based amine oxides having 8 to 30 carbon atoms in the alkyl chain. Commercially available examples are the Tomamine AO types (Air products) and the Genamineox types (Clariant).

The aqueous compositions of the present invention preferably comprise the optional nonionic surfactant in amount of from about 0.05% to about 15%, preferably from about 0.05% to about 5%, still more preferably from about 0.1% to about 5%, specifically from 0.1 to 3% by weight of the composition.

Preferred examples for betaine emulsifiers are carbobetaine, sulfobetaine, phosphatobetaine and phosphonatobetaine groups containing linear or branched C8 to C50, preferred C8 to 40, more preferred C8 to C30 alkyl, fatty alcohol and fatty acid based emulsifiers, i.e. cocoamidopropyl carbobetaines.

Preferably, suitable betaine surfactants for use in compositions according to the invention include those which are known for use in shampoo or other personal care cleansing. They include those surfactants broadly described as derivatives of aliphatic secondary and tertiary amines in which the aliphatic radical can be straight or branched chain and wherein one of the aliphatic substituents contains from about 8 to about 30 carbon atoms and one contains an anionic group such as carboxy, sulfonate, sulfate, phosphate, or phosphonate. Exemplary amphoteric surfactants for use in the formulations of the present invention include cocoamphoacetate, cocoamphodiacetate, lauroamphoacetate, lauroamphodiacetate, and mixtures thereof. They also include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 30 carbon atoms and one contains an anionic group such as carboxy, sulfonate, sulfate, phosphate or phosphonate.

Preferred carbobetaine surfactants are saturated or unsaturated fatty acid based sarcosides having 10 to 18 carbon atoms in the alkyl chain. A commercially available example is Medialan LD (Clariant).

Preferred carbobetaine surfactants are saturated or unsaturated fatty acid based amido propyl betaines having 10 to 18 carbon atoms in the alkyl chain. A commercially available example is Genagen CAB (Clariant).

Preferred sulfobetaine surfactants are saturated or unsaturated fatty acid based taurides having 10 to 18 carbon atoms in the alkyl chain. A commercially available example is Hostapon CT (Clariant).

Details on betaine surfactants are disclosed in US2015/011449.

The compositions of the present invention preferably comprise the optional betaine surfactant in amount of from about 0.05% to about 15%, preferably from about 0.05% to about 5%, still more preferably from about 0.1% to about 5%, specifically from 0.1 to 3% by weight of the composition.

Preferred examples for anionic emulsifiers are carboxylate, sulfate, sulfonate, phosphate and phosphonate groups containing linear or branched C8 to C50, preferred C8 to 40, more preferred C8 to C24 alkyl, fatty alcohol and fatty acid based emulsifiers, i.e. C8 to C24 fatty acid carboxylates, C8 to C24 fatty acid polyether carboxylates, C8 to C24 fatty acid polyether sulfates, C8 to C24 maleic acid addition products, C8 to C24 fatty alcohol sulfates, C8 to C24 sulfonates, C8 to C40 phosphates containing one or two fatty acid moieties.

Preferably, anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is sodium lauryl sulfate or sodium laureth sulfate (sodium lauryl ether sulfate).

Preferred anionic surfactants are saturated or unsaturated fatty alcohol based polyether sulfates having 10 to 18 carbon atoms in the alkyl chain and 2 to 30 EO units. Commercially available examples are the Emulsogen EPM types (Clariant).

Preferred anionic surfactants are saturated or unsaturated fatty alcohol based polyether carboxylates having 10 to 18 carbon atoms in the alkyl chain and 2 to 30 EO units.

Commercially available examples are the Empicol types (Huntsman).

Details on anionic surfactants are disclosed in US2015/011449.

Further details on soaps (in particular salts of fatty acids, such as sodium or potassium or calcium salts of C6 to C22 fatty acids).

The compositions of the present invention preferably comprise the optional anionic surfactant in amount of from about 0.05% to about 15%, preferably from about 0.05% to about 5%, still more preferably from about 0.1% to about 5%, specifically from 0.1 to 3% by weight of the composition.

Further details on surfactants are disclosed in US 2009-0165812.

Preferred examples for the optional silicone based emulsifiers are cationic, nonionoic, betaine and anionic emulsifiers.

Preferred examples for cationic emulsifiers are quaternary ammonium groups containing emulsifiers of the ABA type with EO/PO moieties attached to the terminal quat (quaternary ammonium cation comprising) ends of a silicone chain (WO2009/042083) or quaternized emulsifiers having polyether moieties attached to the silicone chain in a comb like arrangement (US2008/213208).

In another preferred embodiment of the invention hydrophilic polyhydroxy moieties as well as oleophilic fatty alkyl or fatty alkyl ester moieties are attached to the silicone chain (US2012/289649). A commercially available example for this type of W/0 emulsifier is Silform EOF (Momentive Performance Materials).

The compositions of the present invention preferably comprise the optional silicone based cationic surfactant in amount of from about 0.05% to about 15%, preferably from about 0.05% to about 5%, still more preferably from about 0.1% to about 5%, specifically from 0.1 to 3% by weight of the composition.

Preferred examples for siloxane based nonionic emulsifiers are ethylene oxide (EO), propylene oxide (PO) and butylene oxide (BO) containing emulsifiers of the ABA type with EO/PO/BO moieties attached to the terminal ends of a silicone chain or emulsifiers having polyether moieties attached to the silicone chain in a comb like arrangement. A commercially available example is SF 1540 (Momentive Performance Materials). In another preferred embodiment of the invention hydrophilic polyether moieties as well as oleophilic alkyl chains are attached to the silicone chain (U.S. Pat. No. 4,698,178). In another preferred embodiment of the invention hydrophilic polyglycerol moieties as well as alkyl or fatty alcohol ether/fatty acid ester moieties are attached to the silicone chain (US2010/0266651, US2009/0062459). In another preferred embodiment of the invention amodimethicone glycerocarbamates are used (Seidel, SÖFW-Journal, 132, 12-2006, 30). In another preferred embodiment of the invention cetyl diglyceryl tris(trismethylsiloxy)silylethyl dimethicones are used (http://ec.europa.eu/consumers/cosmetics/cosinWindex.cfm?fuseaction=search.details v2&id=92003). The latter four types of emulsifier are especially preferred for W/0 emulsions.

The compositions of the present invention preferably comprise the optional silicone based nonionic surfactant in amount of from about 0.05% to about 15%, preferably from about 0.05% to about 5%, still more preferably from about 0.1% to about 5%, specifically from 0.1 to 3% by weight of the composition.

The compositions of the present invention preferably comprise the optional silicone based betaine and anionic surfactant in amount of from about 0.05% to about 15%, preferably from about 0.05% to about 5%, still more preferably from about 0.1% to about 5%, specifically from 0.1 to 3% by weight of the composition.

It is within the scope of the invention to use more than one surfactant in order to optimize the formulation stability. The total amount on surfactants in the compositions of the present invention preferably ranges from about 0.05% to about 15%, preferably from about 0.05% to about 5%, still more preferably from about 0.1% to about 5%, specifically from 0.1 to 3% by weight of the composition.

In a further embodiment of the invention the aqueous compositions optionally comprise additional additives, such as
a) organic diluents or solvents,
b) proteins, preferably keratin,
c) emollients or fatty substances,
d) preservatives,
e) skin protecting ingredients,
f) conditioning agents,
g) oxidizing agents,
h) reducing agents,
i) tannins,
j) metal salts,
k) further auxiliaries selected from pH adjusting agents, thickeners, lipids, amino acids, sugars, fragrances, sunscreen agents, vitamines, pearlescent agents, gelling agents, trace elements, sequestering agents, antioxidants, humectants, anti-hair loss agents, anti-dandruff agents, propellants, ceramides, polymers, in particular film-forming polymers, fillers, nacres, colorants, in particular pigments and dyes, and mixtures thereof, with the proviso that oxidizing agents and reducing agents are not present simultaneously in a given formulation.

Preferably, the aqueous composition has the following composition:

| Ingredient | Weight-% |
| --- | --- |
| polyorganosiloxane (A) and/or compound (B) as defined above | 0.05 to 30%, preferably 0.1 to 20%, more preferably 0.5 to 15%, more preferably 1 to 10% |
| hydrocarbon or silicone based surfactant | 0 to 15%, preferably 0.05 to 5% |
| Water | q.s. to add to 100% |
| diluents/solvents | 0 to 95, preferably 0.1 to 95%, preferred 10 to 95%, more preferred 20 to 95%, even more preferred 20 to 50% and 50 to 95% |
| protein, preferred keratin | 0 to 15, preferably 0 to 10, such as 0.01 to 5 |
| emollients/fatty substance | 0 to 15, preferably 0 to 10, more preferred 0 to 5%, such as 0.01 to 5% |
| preservatives | 0 to 5, preferably 0 to 3, more preferred 0 to 2%, such as 0.01 to 2.5% |
| skin protecting ingredients | 0 to 15%, preferred 0 to 10%, more preferred 0 to 5%, even more preferred 0 to 1%, specifically 0 to 0.1%, e.g. 0.01 to 5% |
| conditioning agents | 0 to 15%, preferred 0 to 10%, more preferred 0 to 5%, even more preferred 0 to 1%, specifically 0 to 0.1%, e.g. 0.01 to 5% |
| oxidizing agents agents | 0 to 15%, preferred 0 to 10%, more preferred 0 to 5%, even more preferred 0 to 2%, e.g. 0.01 to 5% |
| reducing agents | 0 to 15%, preferred 0 to 10%, more preferred 0 to 5%, even more preferred 0 to 2%, e.g. 0.01 to 5% |
| tannins | 0 to 15%, preferred 0 to 10%, more preferred 0 to 5%, even more preferred 0 to 2%, e.g. 0.01 to 5% |
| metal salts, | 0 to 15%, preferred 0 to 10%, more preferred 0 to 5%, even more preferred 0 to 2%, e.g. 0.01 to 5% |
| hair dyeing agent | 0 to 15%, preferred 0 to 10%, more preferred 0 to 5%, even more preferred 0 to 2%, e.g. 0.01 to 5% |
| other auxiliary agents | 0 to 15%, preferred 0 to 10%, more preferred 0 to 5%, even more preferred 0 to 2%, e.g. 0.01 to 5% | wherein the wt-percentages relate to the total weight of the aqueous compositions.

Diluents/Solvents

The term "diluents/solvents" refers to substances that may be used to dilute/solvatize the at least one polyorganosiloxane A) and/or the at least one organic compound B) according to the invention and the other optional other ingredients as mentioned before in addition to water. Suitable organic solvents are i.e. 2-methyl-1,3-propanediol, mono and dialcohols or the ethers and esters thereof, in particular mono-C1-C3-alkyl ether, ethanol, n-propanol, isopropyl alcohol, tert.butanol, 1-methoxypropanol, 1-ethoxypropanol and ethoxydiglycol, diols and their ethers and esters, 1,3 propanediol, 1,3- and 1,4-butanediol, pentylene glycol, hexylene glycol, diethyleneglycol and the monomethyl and monoethyl ether thereof, dipropylene glycol and the monomethyl and monoethyl ether thereof, glycerol, diglycerol, hexanetriol, sorbitol, ethyl carbitol, benzyl alcohol, benzyloxy ethanol, propylene carbonate, N-alkyl pyrrolidone. In a preferred embodiment water/ethanol, water/isopropyl alcohol, water/dipropylene glycol and water propylene glycol mono methyl ether mixtures are used. Generally, the addition of certain amounts of short chained alcohols improves the homogeneity of the formulations and the penetration of the formulations into the hair. Depending on the polymer structure type and the application purpose certain quantities on acids, bases and/or short chained alcohols are required in order to get transparent formulations. Suitable acids include inorganic or organic acids, like for example carboxyl acids, like acetic acid, hydrochloric acid, sulfuric acid, phosphoric acid. Suitable bases include aqueous ammonia, alkaline hydroxides, alkaline carbonates, etc.

Protein/Keratin

The optional protein, preferred keratin protein fractions used comprise hydrolyzed keratin produced by alkaline and/or enzymatic hydrolysis using methods known in the art. The keratin hydrolysate is about 1,000-3,000 molecular weight. The keratin may be derived from human or other mammalian sources such as goat hair (US 2007-0048235), hoof or horn meals, (U.S. Pat. No. 6,555,505). Alternatively, "keratin protein fraction" is a purified form of keratin that contains predominantly, although not entirely, one distinct protein group as described in U.S. Pat. No. 7,148,327. Details on the keratin and keratin fractions are disclosed in US 2009-0165812.

Emollients, Fatty Substances

A further optional ingredient of the hair treatment formulations is one or more emollients. An "emollient" is a material that protects against wetness or irritation, softens, soothes, supples, coats, lubricates, moisturizes, protects and/or cleanses the skin. Emollients used comprise one or more of: a silicone compound, i.e. dimethicones, cyclomethicones, preferred $D_5$ and $D_6$ cyclosiloxanes, dimethicone copolyols or mixtures of cyclomethicones and dimethicone/vinyldimethicone cross polymer), polyols such as sorbitol, glycerin, propylene glycol, ethylene glycol, polyethylene glycol, caprylyl glycol, polypropylene glycol, 1,3-butane diol, hexylene glycol, isoprene glycol, xylitol, ethylhexyl palmitate, a triglyceride such as caprylic/capric triglyceride and fatty acid ester such as cetearyl isononanoate or cetyl palmitate. Details on emollients are disclosed in US 2009/0165812.

As fatty substances that are liquid at ambient temperature, often referred to as oils, that can be used in the invention, mention may be made of: hydrocarbon-based oils of animal origin, such as perhydrosqualene, hydrocarbon-based plant oils, such as liquid triglycerides of fatty acids containing 4 to 10 carbon atoms, for instance heptanoic or octanoic acid triglycerides, or else sunflower oil, maize oil, soya oil, grapeseed oil, sesame oil, apricot oil, macadamia oil, castor oil, avocado oil, caprylic/capric acid triglycerides, jojoba oil, shea butter; linear or branched hydrocarbons of mineral or synthetic origin, such as liquid paraffins and derivatives thereof, petroleum jelly, polydecenes, hydrogenated polyisobutene such as Parleam®; synthetic esters and ethers, in particular of fatty acids, for instance purcellin oil, isopropyl myristate, 2-ethylhexyl palmitate, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate, triisocetyl citrate, fatty alcohol heptanoate, octanoate and decanoate; polyol ester, for instance propylene glycol dioctanoate, neopentyl glycol diheptanoate, diethylene glycol diisononanoate, pentaerythritol esters, fatty alcohols having 12 to 26 carbon atoms, for instance octyldodecanol, 2-butyloctanol, 2-hexyldecanol, 2-undecyl pentadecanol, oleyl alcohol, partially hydrocarbon-based and/or silicone-based fluoro oils, silicone oils, for instance volatile or non-volatile, linear or cyclic polydimethylsiloxanes (PDMS) which are liquid or pasty at ambient temperature (25° C.), such as cyclomethicones, dimethicones, optionally comprising a phenyl group, for instance phenyl trimethicones, phenyl trimethylsiloxydiphenylsiloxanes, diphenylmethyl-dimethyltrisiloxanes, diphenyl dimethicones, phenyl dimethicones, polymethylphenylsiloxanes; mixtures thereof. Details on suitable fatty substances are disclosed in WO 2012-038334.

Preservatives

Optionally, one or more preservatives may be included in the hair treatment formulations. Examples of such preservatives comprise one or more glycerin containing compound (e.g., glycerin or ethylhexylglycerin or phenoxyethanol), lactic acid, benzyl alcohol, EDTA, potassium sorbate and/or grapefruit seed extract. In a preferred embodiment, the hair straightening formulations are paraben free. Details on preservatives are disclosed in US 2009/0165812.

Skin Protecting Agents

Optionally, the hair treatment formulations comprise one or more skin protecting agents. Skin protecting agents comprise one or more agents that prevent the undesired transmission of microbes or organic/inorganic chemicals. Details on skin protecting agents are disclosed for examples in US 2009/0165812.

Conditioning Agents

Optionally, one or more conditioning agent may be included in the hair treatment formulations. In one preferred embodiment silicone based conditioning agents are incorporated. Preferred materials are PDMS grades ranging from 10 to 1.000.000 mPa·s, C2 to C18-alkyl derivatized silicones, dimethiconols, polyether modified silicones, amino groups or quaternized ammonium groups containing silicones. They may be also selected from polyorganosiloxanes having functional groups FA as defined above. These silicones can be incorporated as neat materials, organic solutions, emulsions or microemulsions.

Preferred examples for quaternary ammonium groups (quats) containing conditioning agents are α,ω-quat group terminated silicones (U.S. Pat. No. 4,891,166), quat group terminated T shaped silicones (US2008027202), α,ω-silicone block terminated quats (WO02/10256) and silicones containing quat groups in a comb like arrangement, optionally containing additional moieties, i.e. polyethers or aromatic structures (US2008213208, U.S. Pat. Nos. 5,098,979, 5,153,294, 5,166,297, US2006188456). Other preferred examples are quat group/silicone block based copolymers (EP282720, U.S. Pat. Nos. 6,240,929, 6,730,766, DE102004002208). In another preferred embodiment quat group/silicone block/hydrophilic block based copolymers are used (WO 02/10257 and WO 02/10259, U.S. Pat. Nos. 7,563,856, 7,563,857, US20110039948, US2007106045, US2005255073, WO2004069137). Other preferred examples are quat group/silicone block based copolymers and quat group/silicone block/hydrophilic block based copolymers bearing terminal monofunctional silicone moieties (WO2013148629, WO2013148635, WO2013148935). In another preferred embodiment of the invention quat group terminated silicones bearing pending amino groups are used (DE10253152). Other preferred examples are silicone betaines (DE10036522, DE10036532). Commercially available examples for quaternary ammonium groups containing siloxanes are Silsoft Silk and Silsoft Q (available from Momentive Performance Materials).

The above described silicone based conditioning agents in particular impart a smooth and silky feel to hair.

Alternatively, hydrocarbon based conditioning agents can be included. Details on these cationic types of material, containing amino and/or quaternary ammonium groups are disclosed for example in US 2009/0000638 and WO 2012/027369.

Oxidizing Agents

Optionally, one or more oxidizing agent may be included in the hair treatment formulations. Preferred oxidizing agents include organic oxidizers, i.e. benzoquinone, other quinone derivatives including hydroquinone and aminoquinones and suitable organic peroxides. Details on organic oxidizers are disclosed in US 2012/0031420 and WO 2012/027369.

Hydrogen peroxide is the preferred inorganic oxidizing agent. Persulfates, in the form of their sodium potassium and ammonium salts, may also be used alone or in combination with the hydrogen peroxide just before use. Other possible oxidizing agents include sodium percarbonate, sodium perborate, magnesium perborate, magnesium dioxide and barium dioxide. Details on these oxidizing agents are disclosed in U.S. Pat. No. 6,544,499.

Reducing Agents

Optionally, one or more reducing agent may be included in the hair treatment formulations with the proviso that oxidizing agents and reducing agents are not present simultaneously in a given formulation. Preferred reducing agents are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycollate, 1,2-propyleneglycol monothioglycollate (see also WO 93/1791), 1-3-propanediol monothioglycollate or the isomer mixture resulting therefrom, 1,3-butanediol and 1,4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof. Details on these organic reducing agents are disclosed in US 2009/0000638.

The usage of inorganic reducing sulfur compounds is basically also possible. Representative examples for use in the reducing compositions include cosmetically acceptable salts (e.g., alkali metal (e.g., sodium and potassium) and ammonium salts), esters (e.g., lower alkyl amines (e.g., triethanolamine (TEA), monoethanolamine (MEA) and aminomethyl propanol (AMP), of sulfite, disulfite, bisulfite, metabisulfite, hydrosulfite, hyposulfite and pyrosulfite). Specific examples of suitable reducing agents thus include sodium metabisulfite, potassium metabisulfite, sodium sulfite, potassium sulfite, sodium thiosulfate, potassium thiosulfate, ammonium bisulfite, ammonium sulfite, ammonium metabisulfite, MEA sulfite, MEA metabisulfite, potassium bisulfite, sodium bisulfite, ammonium bisulfite, sodium hydrosulfite, potassium hydrosulfite, ammonium hydrosulfite, anhydrous sodium sulfite, diammonium sulfite, dipotassium disulfite, dipotassium pyrosulfite, AMP sulfite, AMP metabisulfite, TEA sulfite, TEA metabisulfite, sodium acid sulfite, sodium hyposulfite, sodium pyrosulfite, and sodium thiosulfate pentahydrate. Details on these inorganic reducing agents are disclosed in WO 2012/027369.

Alternatively, high temperature and alkali-treated keratin, wherein the keratin is heated to around 100° C. or above, dithionites and certain hydrides can be used. Details on these reducing agents are disclosed in U.S. Pat. No. 6,544,499.

K) Tannins

Optionally one or more tannins, specifically gallotannins, ellagitannins, complex tannins, condensed tannins, i.e. tannic acid and its other forms quercitannic acid and gallotannic acid may be used. Tannins represent a class of polyphenol derivatives and are known for their structural diversity. A classification is given based on K. Khanbabaee, T. van Ree, Nat. Prod. Rep., 2001, 18, 641-649 which is herewith included by reference and used to define the term tannins in the context of the present invention. The most preferred tannin is gallotannic acid (=tannic acid). Preferred tannins include:

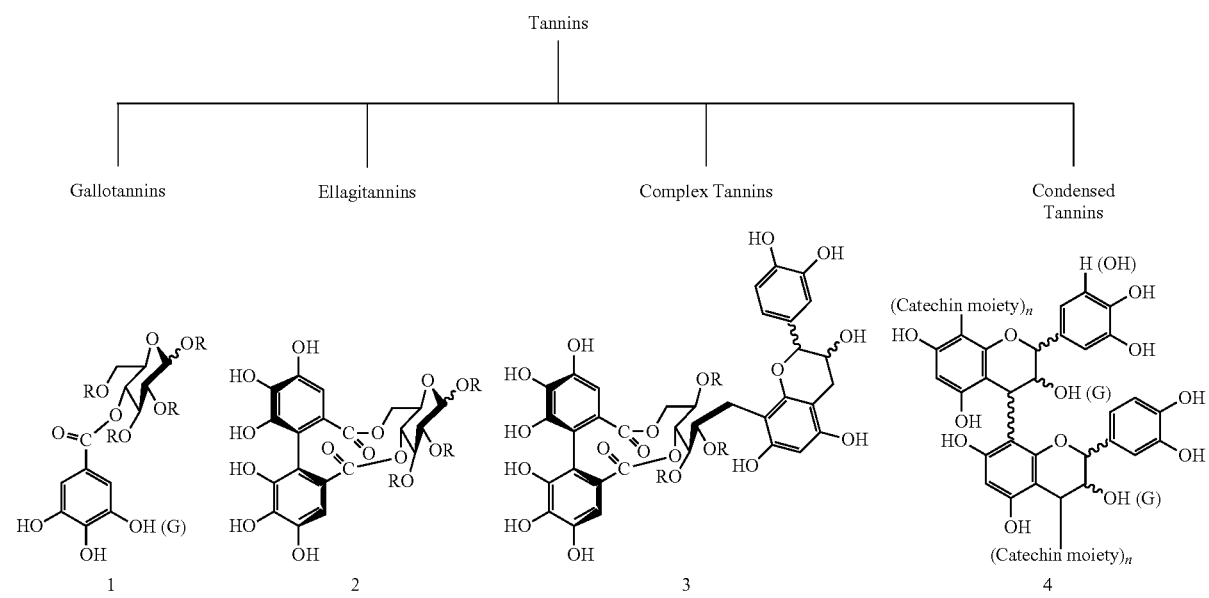

Examples for gallotannins are

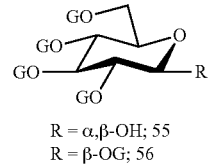

R = α,β-OH; 55
R = β-OG; 56

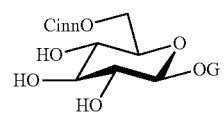

57

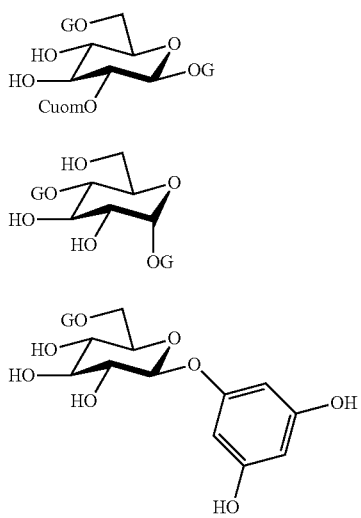
Examples for ellagitannins are
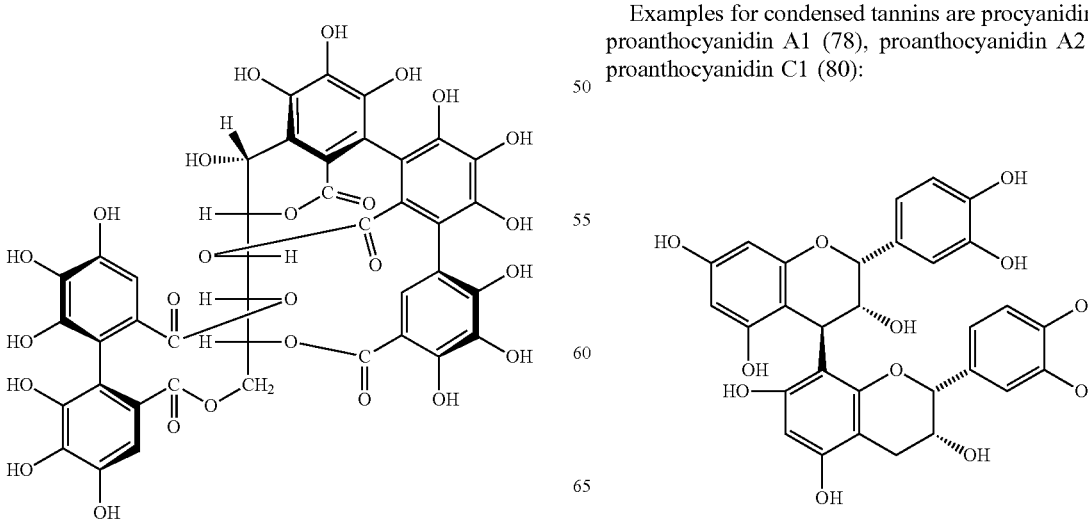
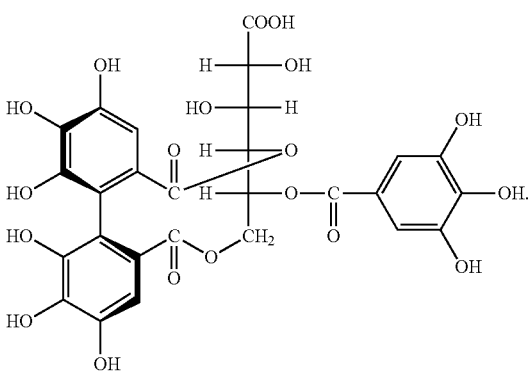
An example for a complex tannin is Acutissimin A
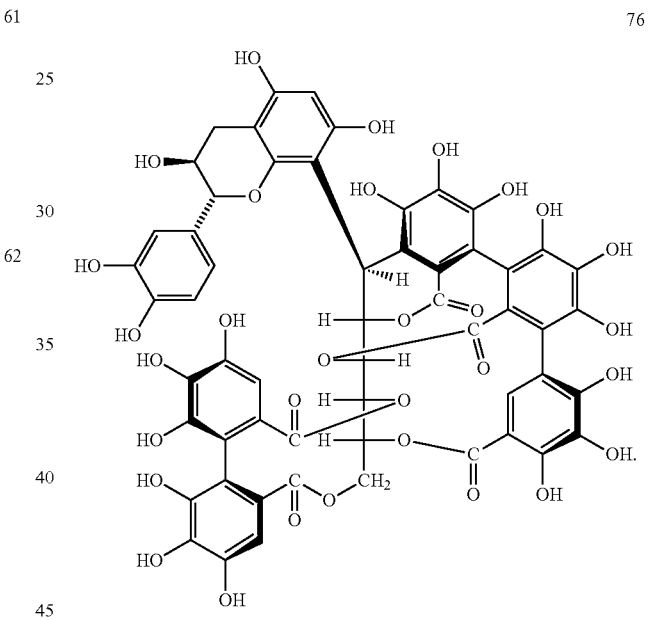
Examples for condensed tannins are procyanidin B2 (77), proanthocyanidin A1 (78), proanthocyanidin A2 (79) and proanthocyanidin C1 (80):

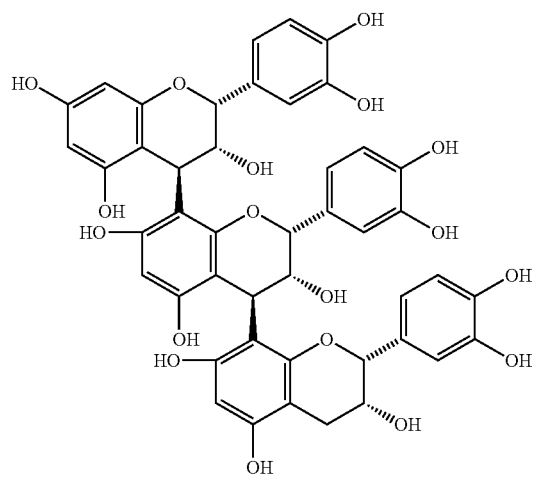
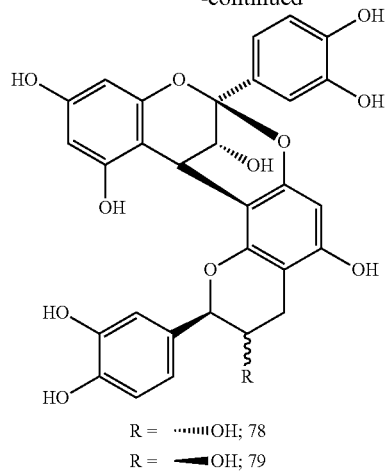
The most preferred tannin is tannic acid:
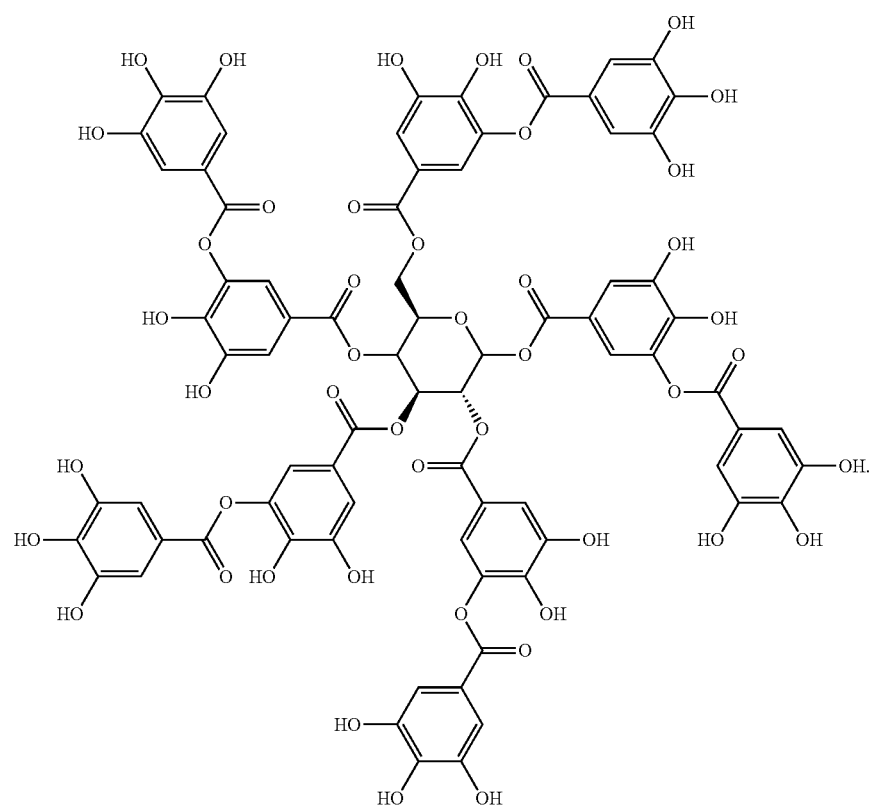 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)C1OC(=O)c1cc(O)c(O)c(OC(=O)c2cc(O)c(O)c(O)c2)c1)c1cc(O)c(O)c(OC(=O)c2cc(O)c(O)c(O)c2)c1]

Metal Salts

Include in particular those of general formula:

$$Me_xA_y$$

wherein Me in this formula is a metal cation and the number of cations Me is x and the number of anions A is y and the numbers x and y are such that the salt is neutral. x may be e.g. 1 or 2, y may be e.g. 1 to 3 in particular. A is preferably (i) the anion of an oxidized carbohydrate of the formula $^-O-C(O)-R$, or an anion derived from an inorganic or organic acid. Me is preferably an iron or zinc cation.

Particular preferred salts are Fe or Zn salts, which are preferably water-soluble, such as $Fe^{2+}$ lactobionate, $Fe^{2+}$ maltobionate, $Fe^{2+}$ isomaltobionate, $Fe^{3+}$ lactobionate, $Fe^{3+}$ maltobionate, $Fe^{3+}$ isomaltobionate, $Fe^{2+}$ gluconate, $Fe^{3+}$ gluconate, $Fe^{2+}$ glucoheptonate, $Fe^{3+}$ glucoheptonate, $Fe^{2+}$ glycerophosphate, $Fe^{3+}$ glycerophosphate, $Zn^{2+}$ lactobionate, $Zn^{2+}$ maltobionate, $Zn^{2+}$ isomaltobionate, $Zn^{2+}$ gluconate, and $Zn^{2+}$ glycerophosphate, $Fe^{2+}$ tartrate, $Fe^{2+}$ glucarate, $Fe^{3+}$ tartrate, $Fe^{3+}$ glucarate, $Zn^{2+}$ tartrate, $Zn^{2+}$ glucarate.

The weight ratio of the optional water soluble Fe and/or Zn salt to the compound according to the invention is at least 0.01, preferred 0.01 to 3, more preferred 0.02 to 3, even more preferred 0.05 to 3, specifically 0.1 to 3, even more specific 0.1 to 1. If the optional tannins are used then the weight ratio of the water soluble Fe and/or Zn salt to the inventive compound plus tannins is at least 0.01, preferred 0.01 to 3, more preferred 0.02 to 3, even more preferred 0.05 to 3, specifically 0.1 to 3, even more specific 0.1 to 1.

The specific amount of water soluble Fe or Zn salt depends on the molecular weight and the structure of the water soluble Fe or Zn salt as well as on molar ratio of the carboxy groups in the inventive compound and the molar amount of the optionally used tannins. Typically, the higher the molecular weight of the water soluble Fe or Zn salt and/or the higher the molar amount of carboxy groups in the inventive organic compounds and the higher the molar amount of optional tannins the higher the specific amount on water soluble Fe or Zn salt used.

Further Auxiliaries

The hair treatment formulations may also comprise one or more additional auxiliaries, i.e. pH adjusting agents, such acids, bases and buffers to adjust the pH value, thickeners (such as polysaccharide thickeners, starch, modified starches, xanthan, gellan, carragenan, pullulan, cellulose, cellulose derivatives, polyacrylic acids, polyacrylates copolymers, polyacrylamides, pectins, clays, fumed silica), lipids, amino acids, sugars, fragrances, sunscreen agents, vitamins, pearlescent agents, gelling agents, trace elements, sequestering agents, antioxidants, humectants, anti-hair loss agents, anti-dandruff agents, propellants, ceramides, polymers, in particular film-forming polymers; fillers, nacres, colorants and in particular pigments and dyes, including hair dyeing agents as described below, all kinds of bioactive phytochemicals, and also mixtures thereof.

Hair Dyeing Agents

Hair dyeing agents include commonly used oxidative or non-oxidative, temporary, semipermanent, demipermanent and permanent hair dyes. Temporary non-oxidative dyes include e.g. Acid Yellow, Acid Orange 7, Acid Yellow 1, Acid Red 33, Acid Red 92, Acid Violet 43, Acid Blue 9, Acid Black 1, which are commonly used in mixtures. Semi-Permanent Non-Oxidative Hair Dyeing Agents contain basic or cationic dyes with low molar mass, and include in particular HO Yellow No. 2, HO Red No. 3, 4-hydroxypropylamino-3-nitrophenol, N,N'-bis-(2-hydroxyethyl)-2-nitrophenylenediamine, HO Blue No. 2, Basic Red 51, Basic Red 76, Basic Brown 16, Basic Brown 17, Basic Blue 99, Basic Yellow 57. Other semipermanent dyes, include metallic and vegetables derivatives (such as Henna). The metallic dyes are derived from silver salts, lead, and bismuth. Permanent Oxidative Hair Dyeing Agents include commonly used complex systems of precursors in the presence of an oxidizing agent. Depending on the polymer structure type and the application purpose certain quantities on acids, bases and/or short chained alcohols are required in order to get transparent formulations. Suitable acids include inorganic or organic acids, like for example carboxylic acids, like acetic acid, hydrochloric acid, sulfuric acid, and phosphoric acid. Suitable bases include aqueous ammonia, alkaline hydroxides, alkaline carbonates, etc.

By adding for example such acids or bases suitable pH ranges of the aqueous compositions can be adjusted such as below 9, preferably below 8.5, preferably below 7.5, more preferably below 7.0.

A further preferred embodiment of the present invention relates to a cosmetic composition or personal care formulation comprising at least one of the polyorganosiloxane (A) and/or at least one of the compound (B) according to the invention, or at least one aqueous composition, each as defined herein, for use in the color and shape treatment of hair, preferably in the color treatment of hair.

Examples of personal care compositions or cosmetic compositions in which the compounds or the invention can be utilized include, but are not limited to, e.g. deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin, combinations of two or more thereof, etc. Such cosmetic or personal care compositions of the present invention may include other ingredients and components as desired for a particular purpose or intended use. For example, personal care compositions may include ingredients chosen from emollient, moisturizer, humectant, pigment, coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, film formers, thickening agents, particulate fillers, silicones, clays, plasticizers, humectants, occlusive, sensory enhancers, esters, resins, film formers, film forming emulsifiers, high refractive index materials, combinations of two or more thereof, etc.

Cosmetic products that can be applied to the face such as skin-care creams, lipsticks, eye and facial makeup, towelettes, and colored contact lenses. Cosmetic products that can be applied to the body such as deodorants, lotions, powders, perfumes, baby products, bath oils, bubble baths, bath salts, and body butters; to the hands/nails: fingernail and toe nail polish, and hand sanitizer; to the hair: permanent chemicals, hair colors, hair sprays, and gels; makeup compositions comprising color pigments, cosmetic products that can applied in particular to the face and eye area such as primers, foundations or eyeshadows, lipsticks, lip gloss, lip liner, lip plumper, lip balm, lip stain, lip conditioner, lip primer, lip boosters, and lip butters which may contain sunscreens, concealers, face powders, mascara, eye shadow, eye liner, eyebrow pencils, creams, waxes, gels, and powders which are used to color, fill in, and define the brows; lotions, cleansing formulations; toners; facial masks; peel masks, sheet masks, exfoliant products, moisturizers such as creams or lotions which may contain essential oils, herbal extracts, or other chemicals; night creams, day creams, sunscreen compositions, nail polishes etc.

Personal care articles, which may comprise the compounds of the invention, include e.g. cosmetic and medical articles, such e.g. bar soap, liquid soap (e.g., hand soap), hand sanitizer (including rinse off and leave-on alcohol based and aqueous-based hand disinfectants), preoperative skin disinfectant, cleansing wipes, disinfecting wipes, body wash, acne treatment products, skin cream, shampoo, conditioner, cosmetics (including but not limited to liquid or powder foundation, liquid or solid eyeliner, mascara, cream eye shadow, tinted powder, "pancake" type powder to be used dry or moistened, etc.) deodorant, antimicrobial creams, body lotion, hand cream, topical cream, aftershave lotion, skin toner, mouth wash, toothpaste, sunscreen lotion, and baby products such as, but not limited to, cleansing wipes, baby shampoo, baby soap, and diaper cream, Wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc. Additional products include but are not limited to oral products such as mouth rinse, toothpaste, and dental floss coatings, veterinary and pet care products, preservative compositions, and surface disinfectants including solutions, sprays or wipes, etc. The aqueous or cosmetic compositions according to the invention can be (used in or) formulated, in particular, into a form typical for hair treatment compositions. Preferred are topical hair care or treatment compositions, e.g. hair tonics, conditioners, hair-care preparations, e.g. pre-treatment preparations, styling creams, styling gels, pomades, hair rinses, treatment packs, intensive hair treatments e.g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hair serums, hair sprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile. Based on the application the hair care preparations may be in particular in the form of a (aerosol) spray, (aerosol) foam, gel, gel spray, cream, lotion, liquid, serum or a wax, mousse, shampoo, such as pearl shampoo, anti-frizz shampoo etc. The aqueous compositions according to the invention can be used as leave-on or rinse-off hair treatment compositions.

A particular preferred cosmetic composition according to the invention is for use in hair treatment, preferably for use in hair coloring treatment. The above described aqueous cosmetic compositions according to the invention can provide particularly benefits with respect to an improved durability of artificial colors on hair. In addition the aqueous hair treatment formulations according to the invention provide a hair strengthening and shaping effect as well as a conditioning effect, in particular, before, during and after a hair dyeing treatment, such as hair bleaching treatment. The hair treatment compositions according to the invention can provide benefits with respect to the strengthening of hair, the hair coloration, the color retention, the color deepening and the shaping of hair, i.e. the curling and straightening of hair.

Preferred cosmetic compositions for the treatment of hair according to the invention are selected from the group consisting of a hair shampoo composition, hair care composition, hair conditioning composition, hair strengthening composition, hair coloration or color deepening or dyeing composition, hair combability improving composition, anti-frizz composition, hair rinse-off and leave-on compositions.

In a further embodiment the invention relates to a process for the treatment of hair which comprises the steps of providing a cosmetic composition according to the invention, and applying said cosmetic composition to said hair. Such process for the treatment of hair may further comprises the step of dyeing the hair.

A particular preferred process for the treatment of hair involves steps of:
1) contacting the hair with the aqueous cosmetic composition of the invention, 2) optionally contacting the hair with an aqueous composition containing a metal salt of Fe and/or Zn, comprising a water phase, having a pH ranging from >2 to 10, and containing water soluble $Zn^{2+}$, $Fe^{2+}$ and/or $Fe^{3+}$ salts with counter ions preferably selected from chloride, sulphate, alkylsulphonate, arylsulphonate, alkylarylsulphonate, hydroxy functionalized carboxylic acids, specifically selected from C2 to C12, preferred C2 to C9 saturated or unsaturated hydroxyalkyl carboxylic acids, i.e. glycolic acid, lactic acid, β-hydroxy butyric acid, γ-hydroxy butyric acid, 2-hydroxysuccinic acid, citric acid, mandelic acid, C2 to C12, preferred C2 to C9, also preferred C7 to C12, more preferred C7 to C9 saturated or unsaturated polyhydroxyalkyl carboxylic acids, i.e. glyceric acid, 2,2-dimethylolpropane carboxylic acid, arabinonic acid, gluconic acid, glucoronic acid, glucoheptonic acid, glucopyranosyl arabinonic acid, lactobionic acid, maltobionic acid, tartaric acid, glucaric acid, C7 to C12, preferred C7 to C9 hydroxyaromatic carboxylic acids, i.e. 2-hydroxy benzoic acid, 3-hydroxy benzoic acid, 4-hydroxy benzoic acid, 2-hydroxy cinnamic acid, 3-hydroxy cinnamic acid, 4-hydroxy cinnamic acid, C7 to C12, preferred C7 to C9 polyhydroxyaromatic carboxylic acids, i.e. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, dihydroxy cinnamic acids or their partial esters, i.e. 3,4-dihydroxy cinnamic acid, trihydroxy benzoic acids or their partial esters, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, trihydroxy cinnamic acids or their partial esters, i.e. 3,4,5-dihydroxy cinnamic acid, and mixtures thereof, and 3) drying the hair at a temperature of preferably >150° C., for example during a hot ironing step, which permanently bonds to the hair or incorporates into the hair the inventive hair treatment compositions or parts of the hair treatment composition used in steps 1) and 2).

Another particular preferred process for the treatment of hair involves steps of:

1) contacting the hair with the aqueous cosmetic composition of the invention, comprising the compound of the invention, optionally one more surfactants as explained above, and a metal salt of Fe and/or Zn, preferably water-soluble $Zn^{2+}$, $Fe^{2+}$ and/or $Fe^{3+}$ salts with counter ions preferably selected from chloride, sulphate, alkylsulphonate, arylsulphonate, alkylarylsulphonate, hydroxy functionalized carboxylic acids, specifically selected from C2 to C12, preferred C2 to C9 saturated or unsaturated hydroxyalkyl carboxylic acids, i.e. glycolic acid, lactic acid, β-hydroxy butyric acid, γ-hydroxy butyric acid, 2-hydroxysuccinic acid, citric acid, mandelic acid, C2 to C12, preferred C2 to C9, also preferred C7 to C12, more preferred C7 to C9 saturated or unsaturated polyhydroxyalkyl carboxylic acids, i.e. glyceric acid, 2,2-dimethylolpropane carboxylic acid, arabinonic acid, gluconic acid, glucoronic acid, glucoheptonic acid, glucopyranosyl arabinonic acid, lactobionic acid, maltobionic acid, tartaric acid, glutaric acid C7 to C12, preferred C7 to C9 hydroxyaromatic carboxylic acids, i.e. 2-hydroxy benzoic acid, 3-hydroxy benzoic acid, 4-hydroxy benzoic acid, 2-hydroxy cinnamic acid, 3-hydroxy cinnamic acid, 4-hydroxy cinnamic acid, C7 to C12, preferred C7 to C9 polyhydroxyaromatic carboxylic acids, i.e. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, dihydroxy cinnamic acids or their partial esters, i.e. 3,4-dihydroxy cinnamic acid, trihydroxy benzoic acids or their partial esters, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, trihydroxy cinnamic acids or their partial esters, i.e. 3,4,5-dihydroxy cinnamic acid, and mixtures thereof, and 2) Drying the hair at >150° C., e.g. during a hot ironing step, which permanently bonds to the hair or incorporate into the hair the inventive hair treatment composition or parts of the hair treatment composition used in step 1).

In the above processes the weight ratio of the optional water soluble Fe and/or Zn salt to the compound according to the invention is at least 0.01, preferred 0.01 to 3, more preferred 0.02 to 3, even more preferred 0.05 to 3, specifically 0.1 to 3, even more specific 0.1 to 1. If the optional tannins are used then the weight ratio of the water soluble Fe and/or Zn salt to the inventive compound (polyorganosiloxane of formula (A) and/or compound of formula (B)) plus tannins is at least 0.01, preferred 0.01 to 3, more preferred 0.02 to 3, even more preferred 0.05 to 3, specifically 0.1 to 3, even more specific 0.1 to 1. The specific amount of water soluble Fe and/or Zn salt depends on the molecular weight and the structure of the water soluble Fe or Zn salt as well as on molar ratio of the carboxy groups in the inventive compound and the molar amount of the optionally used tannins. Typically, the higher the molecular weight of the water soluble Fe or Zn salt and/or the higher the molar amount of carboxy groups in the inventive organic compounds and the higher the molar amount of optional tannins the higher the specific amount on water soluble Fe or Zn salt used.

Preferably, process step 1), contacting the hair with the aqueous cosmetic composition of the invention, to form treated hair is carried out at a temperature and length of time sufficient to penetrate the fiber. Typically, process step 1) is carried out at 10 to 50° C., preferred at 20 to 50° C., even more preferred room temperature, for 5 to 120 min, preferred 5 to 60 min, even more preferred 10 to 40 min.

Preferably, process step 2), contacting the hair with the inventive hair treatment compositions based on water soluble $Zn^{2+}$, $Fe^{2+}$ and/or $Fe^{3+}$ salts to form further treated hair is carried out at a temperature and length of time sufficient to penetrate the fiber. Typically, process step 2) is carried out at 10 to 50° C., preferred at 20 to 50° C., even more preferred room temperature, for 5 to 120 min, preferred 5 to 60 min, even more preferred 10 to 40 min.

Preferably, process step 3) drying the treated hair by applying heat with a temperature of >150° C., preferably is a hot ironing step which permanently bonds to the hair or incorporates into the hair the inventive hair treatment compositions or parts of the hair treatment compositions used in steps 1) and 2). The elevated temperature can result in chemical reactions of components of the compositions used in steps 1) and 2) with reactive moieties of the keratin fiber or the formation of complexes of components of the compositions used in steps 1) and 2). Preferred temperatures range from 150° C. to about 235° C., more preferred from 180° C. to about 225° C., even more preferred from 190° C. to about 215° C. Typically, 2 to 10 rounds of hot ironing are applied in case of drying the hair.

In the context of the present invention water soluble Zn and/or Fe salts used in step 2) preferably have a water solubility of at least 0.5 g/l at 25° C.

In a preferred embodiment the aqueous compositions used according to the invention comprise at least one metal salt such as Zn and/or Fe salts in particular as described above. The above described hair treatment process according to the invention can provide benefits with respect to the strengthening of hair, the hair shaping, i.e. the curling and straightening of hair, the hair coloration, the hair bleaching, the hair color retention, the hair color deepening, the hair conditioning.

The present invention further relates to the use of the aqueous compositions according to the invention for the treatment of hair, in particular, in the color and shape treatment of hair, e.g. for strengthening of hair, for hair color retention, for hair color enhancement, for hair color deepening, for hair color protection, for shaping of hair, i.e. the curling and straightening of hair, for hair conditioning, for hair smoothening or softening, for hair straightening, for improving manageability of the hair, in particular for improving the combability of the hair.

Most preferred cosmetic compositions according to the invention are for use in hair treatment, preferably for use in hair coloring.

Most preferred cosmetic compositions according to the invention are selected from a hair shampoo composition, hair care composition, hair conditioning composition, hair strengthening composition, hair coloration or dyeing composition, hair combability improving composition, anti-frizz composition, hair rinse-off and leave-on compositions.

The present invention further relates to the use of the polyorganosiloxane of formula (A) and/or the compound of formula (B) according to the invention or the aqueous composition according to the invention for the treatment of hair, preferably for strengthening of hair, for hair color retention, for hair color enhancement, for hair color deepening, for hair color protection, for shaping of hair, i.e. the curling and straightening of hair, for hair conditioning, for hair smoothening or softening, for hair straightening, for improving manageability of the hair, in particular for improving the combability of the hair.

In a preferred embodiment of the aqueous composition according to the invention comprises at least one hair dyeing agent. Preferably the aqueous composition according to the invention is selected from a hair shampoo composition, hair care composition, hair condition composition, hair strengthening composition, hair coloration or dyeing composition, hair color deepening composition, hair combability improving composition, anti-frizz composition, hair rinse-off and leave-on compositions.

In a preferred embodiment of the aqueous composition according to the invention is for use in the color treatment of hair, such as in hair color retention treatment, for hair color enhancement treatment, for hair color deepening treatment, or for hair color protection treatment.

In a preferred embodiment of the present invention relates to a process for the color treatment of hair which comprises the steps of providing an aqueous compositions according to the invention, and applying said aqueous compositions to said hair.

A preferred embodiment of the present invention relates to a process for the color treatment of hair which comprises the steps of providing an aqueous compositions according to the invention, and applying said aqueous compositions to said hair, and the step of dyeing the hair.

A further preferred embodiment of the present invention relates to a compound (B) of the formula:

$$R^2(-F)_{2\text{-}18}$$

wherein
$R^2$ is selected from divalent to octadecavalent, optionally substituted hydrocarbon radicals which have up to 100 carbon atoms, and may contain optionally one or more groups selected from $-O-$, $-NH-$, $-C(O)-$, $-C(S)-$, tertiary amino groups

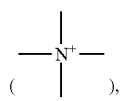

and quaternary ammonium groups

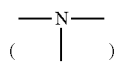

and
F is selected from:

$$-O-C(O)-R^3-C(O)OH, \text{ and}$$

$$-NR^1-C(O)-R^3-C(O)OH,$$

the groups F bind to a carbon atom of $R^2$,
wherein
$R^1$ is selected from the group consisting of hydrogen, or optionally substituted straight-chain, cyclic or branched, saturated, unsaturated or aromatic hydrocarbon radicals which have up to 100 carbon atoms which optionally contain one or more groups selected from $-O-$, $-NH-$, $-C(O)-$, $-C(S)-$, tertiary amino groups

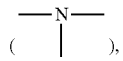

and quaternary ammonium groups

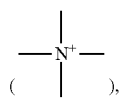

$R^3$ is selected from a single bond or optionally substituted straight-chain, cyclic or branched, saturated, unsaturated or aromatic hydrocarbon radicals which have up to 100 carbon atoms, which optionally contain one or more groups selected from $-O-$, $-NH-$, $-C(O)-$, $-C(S)-$, tertiary amino groups

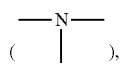

and quaternary ammonium groups

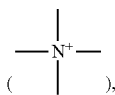

with the proviso that $R^3$ is not —CH=CH—, and salts thereof, and aqueous compostions thereof. Particular preferred compounds (B) have the formula:

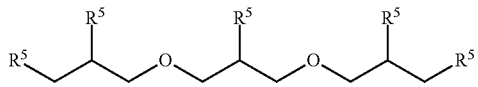

wherein $R^5$ is selected from the group consisting of hydroxy or F, wherein F is as defined above, with the proviso that at least two of $R^5$ are F.

Particular preferred compounds (B) have the formula:

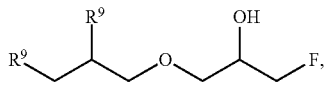

wherein one of $R^9$ is hydroxy and one of $R^9$ is a group of the formula

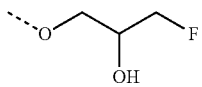

and wherein F is as defined above and the dotted line is the bond to the carbon atom.

A preferred compound (B) according to the invention is a mixture of the following two isomers:

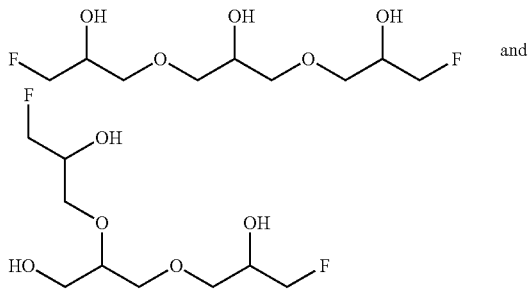

wherein F is as defined above.

A preferred compound (B) according to the invention has the formula:

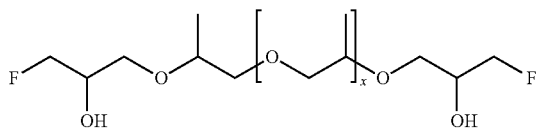

wherein x is from 1 to 10, preferably 1 to 5, and F is as defined above.

In preferred compounds (B) according to the invention $R^3$ is selected from the group consisting of a single bond and straight-chain, cyclic or branched, saturated, unsaturated or aromatic hydrocarbon radicals which have up to 18, preferably up to 12, more preferably up to 10 carbon atoms, and which optionally contain one or more groups selected from —O—, —NH—, —C(O)—, and wherein $R^3$ is optionally substituted by one or more groups selected from hydroxyl groups, amino groups, and carboxy groups. More preferably in the compound (B) $R^3$ is derived from a dicarboxylic acid of the formula:

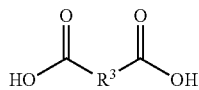

wherein $R^3$ is as defined above, such as optionally substituted aliphatic, saturated or unsaturated or aromatic dicarboxylic acids, such as oxalic acid (ethanedioic acid), malonic acid (propanedioic acid), succinic acid (butanedioic acid), glutaric acid (pentanedioic acid), adipic acid (hexanedioic acid), pimelic acid (heptanedioic acid), suberic acid (octanedioic acid), azelaic acid (nonanedioic acid), sebacic acid (decanedioic acid), undecanedioic acid, dodecanedioic acid, brassylic acid (tridecanedioic acid), thapsic acid (hexadecanedioic acid), glutaconic acid (pent-2-enedioic acid), citraconic acid ((2Z)-2-methylbut-2-enedioic acid), mesaconic acid ((2E)-2-methyl-2-butenedioic acid), itaconic acid (2-methylidenebutanedioic acid), tartronic acid (2-hydroxypropanedioic acid), mesoxalic acid (oxopropanedioic acid), malic acid (hydroxybutanedioic acid), tartaric acid (2,3-dihydroxybutanedioic acid), oxaloacetic acid (oxobutanedioic acid), aspartic acid (2-aminobutanedioic acid), α-hydroxy glutaric acid (2-hydroxypentanedioic acid), arabinaric acid (2,3,4-trihydroxypentanedioic acid), acetonedicarboxylic acid (3-oxopentanedioic acid), α-ketoglutaric acid (2-oxopentanedioic acid), glutamic acid (2-aminopentanedioic acid), diaminopimelic acid ((2R,6S)-2,6-diaminoheptanedioic acid), saccharic acid ((2S,3S,4S,5R)-2,3,4,5-tetrahydroxyhexanedioic acid), phthalic acid (benzene-1,2-dicarboxylic acid), isophthalic acid (benzene-1,3-dicarboxylic acid), terepthtalic acid ((benzene-1,3-dicarboxylic acid)), diphenic acid (2-(2-carboxyphenyl)benzoic acid), 2,6-naphthalenedicarboxylic acid, norbornene dicarboxylic acid, norbornane dicarboxylic acid, and trimellitic acid, or $R^3$ is derived from an aliphatic or aromatic tricarboxylic acid, wherein $R^3$ is substituted with carboxyl group (COOH), such as citric acid (2-hydroxypropane-1,2,3-tricarboxylic acid), isocitric acid (1-hydroxypropane-1,2,3-tricarboxylic acid), aconitic acid ((cis or trans prop-1-ene-1,2,3-tricarboxylic acid), propane-1,2,3-tricarboxylic acid; trimesic acid (benzene-1,3,5-tricarboxylic acid), the reaction products of carboxylic acid anhydrides, such as maleic anhydride and succinic anhydride, with amino acids and amino acid derivatives, such as β-alanine and asparagine, i.e. N-acetyl aspartic acid, N-maleoyl-β-alanine ((E)-4-(2-carboxyethylamino)-4-oxo-but-2-enoic acid), N-maleoyl-asparagine (4-amino-2-[[(E)-4-hydroxy-4-oxo-but-2-enoyl]amino]-4-oxo-butanoic acid).

In preferred compounds (B) according to the invention F is selected from the group consisting of the formulas:

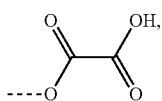

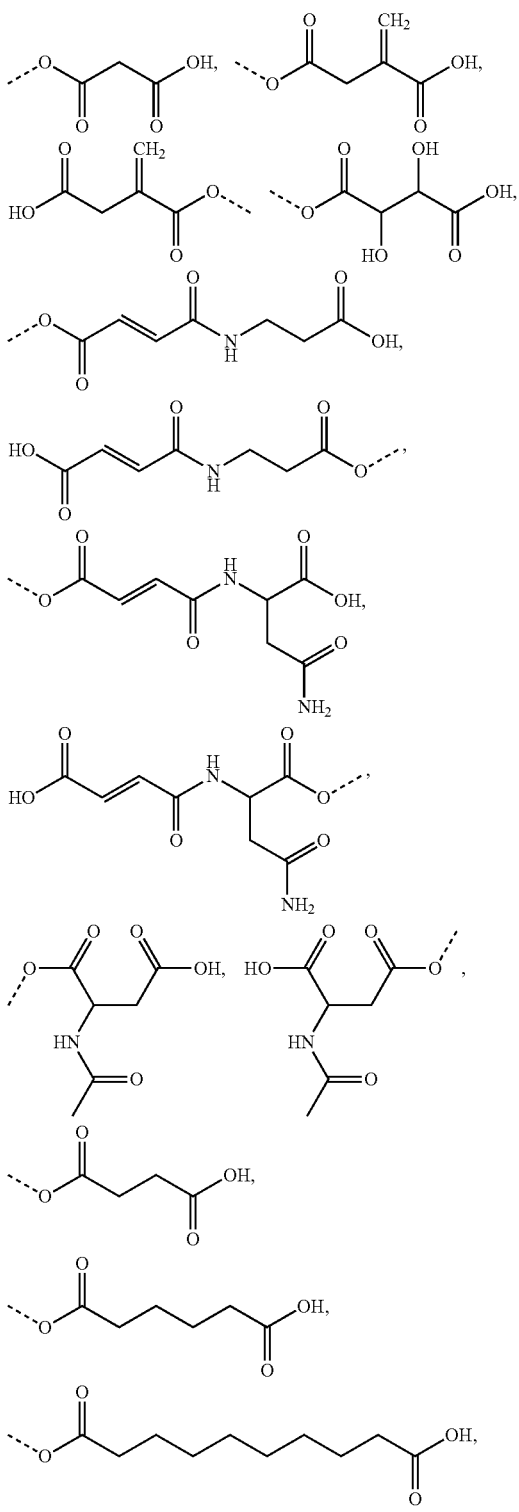

wherein the dotted line in the above formulae represents the bond to the oxygen atom, and wherein there are at least two groups F.

In a further preferred embodiment of the invention it relates to polyorganosiloxanes (A) having an average number of 2 to 1000 siloxy units selected from the siloxy groups of the formulas:

(A)

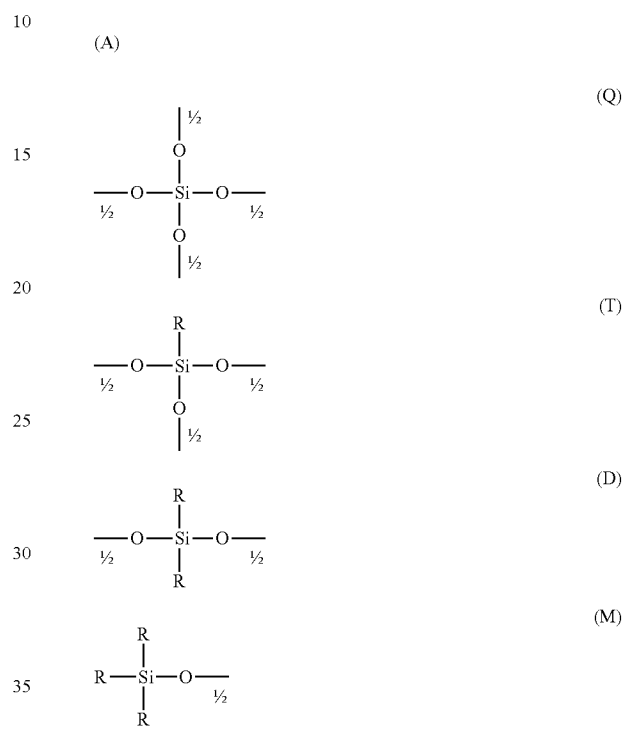

wherein

R is selected from $R^1$ and $R^F$, wherein $R^1$ is selected from organic groups bound to the silicon atoms by a carbon atom, and two groups $R^1$ may form a bridging group between two silicon atoms, $R^F$ is selected from organic groups different from $R^1$ and is bound to the silicon atoms by a carbon atom, and $R^F$ contains at least one functional group F selected from:

O—C(O)—$R^3$—C(O)OH, and

—$NR^4$—C(O)—$R^3$—C(O)OH, and wherein the groups F bind to a carbon atom, wherein $R^3$ is selected from a single bond or optionally substituted straight-chain, cyclic or branched, saturated, unsaturated or aromatic hydrocarbon radicals which have up to 100 carbon atoms, which optionally contain one or more groups selected from —O—, —NH—, —C(O)—, —C(S)—, tertiary amino groups

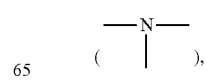

and quaternary ammonium groups $$-\overset{|}{\underset{|}{N^+}}-$$
( ), with the proviso that R³ is not —CH=CH— or —CH₂—CH₂—, and R⁴ is selected from the group consisting of hydrogen, or optionally substituted straight-chain, cyclic or branched, saturated, unsaturated or aromatic hydrocarbon radicals which have up to 100 carbon atoms which optionally contain one or more groups selected from —O—, —NH—, —C(O)—, —C(S)—, tertiary amino groups $$-\overset{|}{N}-$$
( ), and quaternary ammonium groups $$-\overset{|}{\underset{|}{N^+}}-$$
( ), wherein the preferred substitutent groups have the same meanings as described above, and aqueous compostions thereof.

Aspects of the invention may be further understood with reference to the following non-limiting examples.

EXAMPLES (The percentages refer to weight-% unless otherwise indicated).

Example 1

A Glycerol Diglycidyl Ether Based Succinic Acid Ester Derivative

In a 250 ml three-necked flask, equipped with refluxing condenser, thermometer and magnetic stirrer, 23.1 g (195.8 mmol) succinic acid, 122 g dipropylene glycol and 0.8 g triethylamine are mixed and heated to 90° C. 20 g (195.8 mmol epoxy groups) glycerol diglycidylether (RO—CH₂—CH(OR)—CH₂—OR    R = (1:2) H or *—CH₂—CH(—O—)CH₂ (epoxide))

are added dropwise within 20 minutes. The mixture is kept at 90° C. for 12 hours. Afterwards, the transparent slightly yellow mixture is cooled to room temperature and the conversion of the epoxide groups determined by means of ¹H NMR spectroscopy. The conversion of epoxy groups is 100%.

A product essentially consisting of the following isomers is obtained

Example 2

Glycerol Diglycidylether with Three Succinic Ester Functions

In a 100 ml three-necked flask, equipped with refluxing condenser, thermometer and magnetic stirrer, 10 g (97.9 mmol epoxy groups) of glycerol diglycidylether, 11.56 g succinic acid (97.9 mmol), 61.7 g methoxypropyl acetate and 0.53 g trimethylamine are mixed and heated to 90° C. for 15 hrs. Upon progression of the esterification reaction the mixture turns turbid. The conversion of the epoxide groups, as determined by means of ¹H NMR spectroscopy is 100%.

4.9 g (48.9 mmol) succinic acid anhydride are added and the reaction continued at 90° C. for 6 hrs. Upon progression of this second esterification reaction the mixture turns transparent (slightly brownish). The conversion of the anhydride groups, as determined by means of ¹H NMR spectroscopy, is 100%.

61.7 g 1,3-butanediol are added. The methoxypropyl acetate is removed under reduced pressure at 75° C./3 mm Hg.

A slightly brownish transparent liquid is obtained.

A product essentially consisting of the following isomers is obtained

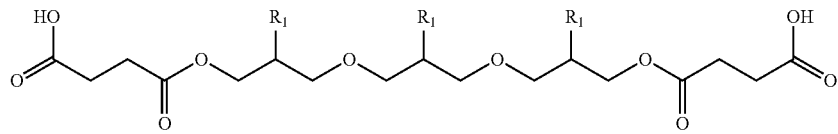

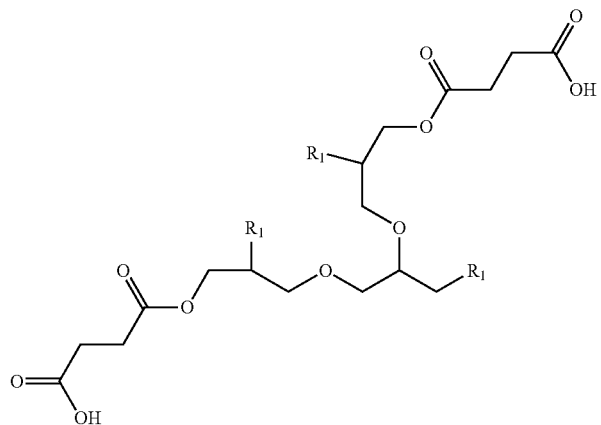

with $R^1$ being —OH and —OC(O)CH$_2$CH$_2$COOH in a ratio of 2:1.

Example 3

A Glycerol Diglycidyl Ether Based Adipic Acid Ester Derivative

In a 100 ml three-necked flask, equipped with refluxing condenser, thermometer and magnetic stirrer, 10 g (97.9 mmol epoxy groups) of glycerol diglycidylether, 14.31 g adipic acid (97.9 mmol), 56.71 g 1,3-butanediol and 0.48 g trimethylamine are mixed and heated to 90° C. for 9.5 hrs. The conversion of the epoxide groups, as determined by means of $^1$H NMR spectroscopy is 99.5%. A colorless transparent liquid is obtained.

A product essentially consisting of the following isomers is obtained:

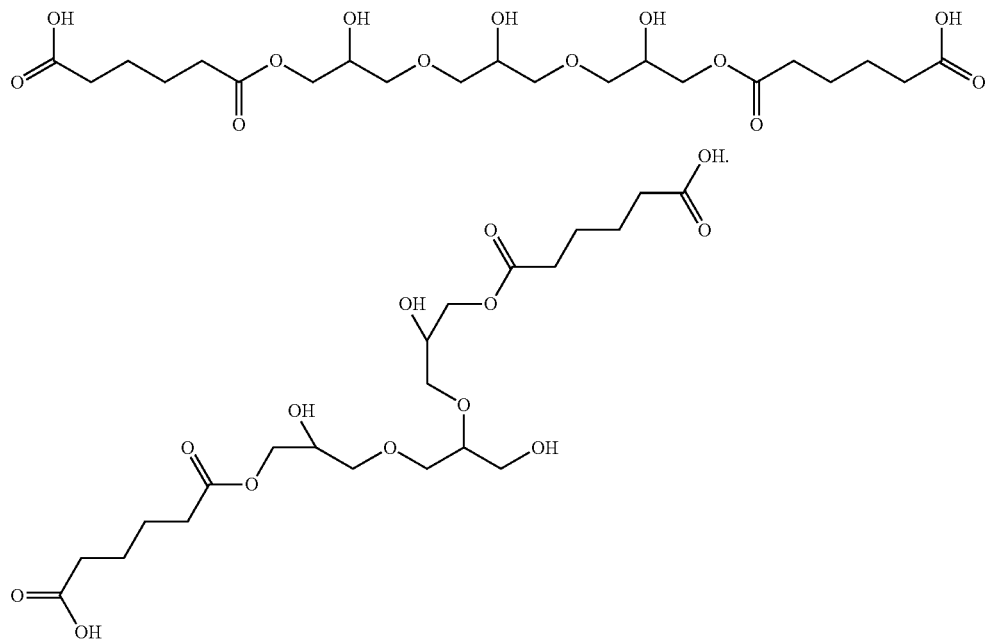

Example 4

Glycerol Diglycidylether with Two Succinic Ester Functions and Two Adipic Acid Ester Functions In a 100 ml three-necked flask, equipped with refluxing condenser, thermometer and magnetic stirrer, 14.31 g adipic acid (97.9 mmol), 56.71 g methoxypropyl acetate and 0.51 g trimethylamine are mixed and heated to 70° C. 10 g (97.9 mmol epoxy groups) of glycerol diglycidylether are added during 15 minutes. The initially turbid mixture turns clear. Afterwards, the temperature is increased to 90° C. and maintained for 11 hrs.

The conversion of the epoxide groups, as determined by means of $^1$H NMR spectroscopy is 99%.

9.79 g (97.9 mmol) succinic acid anhydride are added and the reaction continued at 90° C. for 6.5 hrs. The conversion of the anhydride groups, as determined by means of $^1$H NMR spectroscopy, is 98%. Upon cooling to room temperature the target product precipitates from the solution.

79.6 g 1,3-butanediol are added. The methoxypropyl acetate is removed under reduced pressure at 75° C./3 mm Hg.

A slightly yellowish transparent liquid is obtained.

A product essentially consisting of the following isomers is obtained:

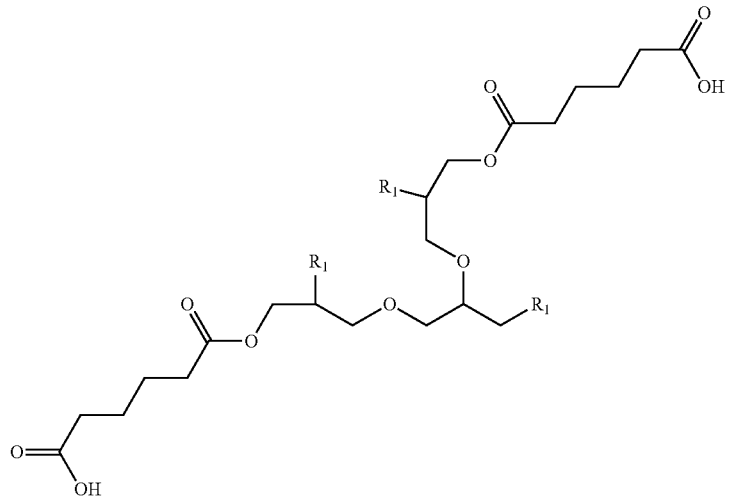

with $R_1$ being —OH and —OC(O)CH$_2$CH$_2$COOH in the ratio of 1:2.

Example 5

A Triglycerol Based Itaconic Acid Ester Derivative

In a 100 ml three-necked flask, equipped with refluxing condenser, thermometer and magnetic stirrer, 60 g methoxypropyl acetate, 10 g (41.6 mmol) triglycerol

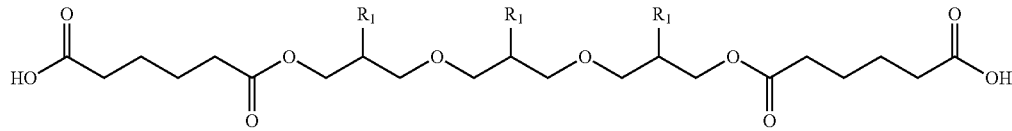

and 0.29 g triethylamine are mixed and heated to 70° C. 9.33 g (83.2 mmol) itaconic acid anhydride are added dropwise within 15 minutes. The mixture is heated to 90° C. for 18 hours. The initially yellow dispersion turns slightly reddish during the course of the reaction. The conversion of the anhydride is determined by means of $^1$H NMR spectroscopy. The conversion of the anhydride is 100%. Afterwards, 60 g 1,3 butanediol are added and the methoxypropyl acetate removed at 70° C./20 mbar during 2 hrs. A slightly yellow transparent solution is obtained.

A product essentially consisting of the following structure

R—O—CH$_2$—CH(OR)—CH$_2$—O—CH$_2$—CH(OR)—CH$_2$—O—CH$_2$—CH(OR)—CH$_2$—O—R with two of the R being:

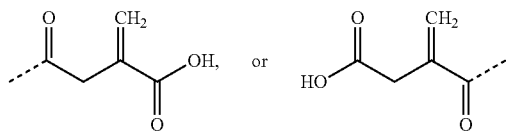

(wherein the dotted line is the bond to the oxygen atom) and three being hydrogen, is obtained.

Example 6

A Glycerol Diglycidyl Ether Based Itaconic Acid Ester Derivative

In a 100 ml three-necked flask, equipped with refluxing condenser, thermometer and magnetic stirrer, 10.76 g (82.7 mmol) itaconic acid, 60 g 1,3 butanediol and 0.29 g triethylamine are mixed and heated to 80° C. 8.45 g (82.7 mmol epoxy groups) glycerol diglycidylether are added dropwise within 20 minutes. The temperature increased to 86° C. It is further increased to 90° C. and kept there for 14 hours. Afterwards, the transparent colorless mixture is cooled to room temperature and the conversion of the epoxide groups determined by means of $^1$H NMR spectroscopy. The conversion of epoxy groups is 100%.

A product essentially consisting of the following isomers is obtained:

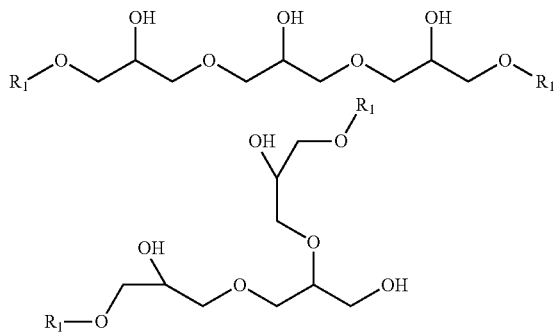

with $R_1$

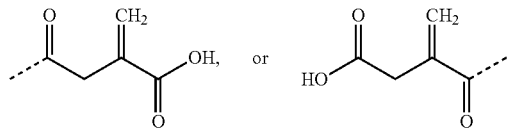

(wherein the dotted line is the bond to the oxygen atom).

Application Tests

Test Method

Test method for evaluation of the color retention is described in detail in US 2011/0219552 A1. The method determines the hair color changes before and after washes by Delta E. Color changes were measured by measuring CIE L*, a* and b* values (or CIELAB color space) on a HunterLab colorimeter.

The meaning of L*, a*, b* was elaborated in "Practical Modern Hair Science" Trefor Evans and R. Randall Wichett, Alluredbooks, Carol Stream, Ill., 2012. The L* value measures the lightness from L*=0 (black) to L*=100 (white). The color is measured by a* from negative value (green) to positive value (red) and b* from negative value (blue) to positive value (yellow). For example, a medium blonde has an L*, a*, b* value of L*=49, a*=12, b*=26 and a medium auburn has an L*, a*, b* value of L*=26, a*=13, b*=12. Delta E was calculated using the following equation to evaluate color change before and after washes.

$$\text{Delta } E = ((L_t^* - L_0^*)^2 + (a_t^* - a_0^*)^2 + (b_t^* - b_0^*)^2)^{1/2}$$

Where $L_0^*$, $a_0^*$, $b_0^*$, and $L_t^*$, $a_t^*$, $b_t^*$ are measured CIE L*, a*, b* color parameters (or CIELAB color space) before and after washing, respectively.

The larger value of Delta E reflects greater change of color, so smaller Delta E is desired because it indicates less color loss after washing.

Similarly, color enhancement was calculated using the following equation to evaluate initial color depth increase with treatment.

$$\text{Delta } E = ((L_2^* - L_1^*)^2 + (a_2^* - a_1^*)^2 + (b_2^* - b_1^*)^2)^{1/2}$$

Where $L_2^*$, $a_2^*$, $b_2^*$, and $L_1^*$, $a_1^*$, $b_1^*$ are measured CIE L*, a*, b* before washing color parameters with and without treatment respectively. Here larger Delta E is desired because it means more initial color enhancement.

Example 7

Example 7.1 Application on Color Enhancement and Color Retention of Single Bleached European Hair The following treatment solution was prepared:

TS1 solution (polyglycerol succinic ester from example 1) approximately 50 ml was composed 3 g of the polyglycerol succinic ester from example 1, 7 g dipropylene glycol (that is 10 g solution of the polyglycerol succinic ester in dipropylene glycol obtained in example 1), and 40 g water.

The hair dye was a commercial hair dye Garnier Nutrisse Ultra Color R3, Light Intense Auburn, from L'Oreal.

Pre-Treatment with Aqueous Solution According to the Invention Before Dyeing of Hair A bundle of 4 g single bleached European hair tress (Kerling International Haarfarbrik GMBH) was immersed in 50 g TS1 solution for 30 minutes. Then the hair was dried at room temperature overnight. The hair bundle was then washed by 10 wt-% SLES (Sodium Lauryl Ether Sulfate) for 3 times. Hair was dried and then dyed with Garnier R3 dye for 30 minutes following the standard dyeing procedure of Garnier R3.

The control tress was the tress treated by 50 ml water. And then washed with 10 wt-% SLES and dyed with Garnier R3 dye same as hair tress treated by crosslinking technology. The initial color was measured.

Post-Treatment with Aqueous Solution According to the Invention after Dyeing of Hair A bundle of 4 g single bleached European hair tress (Kerling International Haarfarbrik GMBH) dyed with Garnier R3 dye for 30 minutes following the standard dyeing procedure of Garnier R3. Then the hair was dried by bonnet. The initial color was measured. The dried hair was immersed in 50 g TS1 solution for 30 minutes. Then the hair was dried at room temperature overnight. The hair bundle was then washed by 10 wt-% SLES (Sodium Lauryl Ether Sulfate) for 3 times. Hair was then dried.

The control tress was Garnier R3 dyed tress treated by 50 ml water. The hair was then washed with 10 wt-% SLES and dried same as hair tress treated by crosslinking technology.

Wash Protocol

The 4 g hair tresses were put in 250 ml conical flask with 200 ml 2.5% SLES solution. The flask was shaked at 120 rpm 42° C. in Shel Lab shaking water bath for 5 minutes, (5 minutes wash equals 10 hand washes.) After 5 minutes, the hair was dried and the hair color was measured.

Pre-Treatment Benefits
Color Enhancement Delta E for Pre-Treatment

|  | Initial Color L*, a*, b* | | | Color Enhancement |
|---|---|---|---|---|
|  | L* | a* | b* | Delta E |
| Control | 24.15 | 27.03 | 15.14 |  |
| TS1 (polyglycerol succinic ester from example 1) | 22.75 | 19.31 | 9.27 | 9.88 |

The hair treated by the technology according to the invention before dyeing shows a color enhancement effect with darker initial color compared to the control.

Color Retention Benefit for Pre-Treatment

|  | Color Loss Delta E |
|---|---|
| Control | 12.50 |
| TS1 ((polyglycerol succinic ester from example 1) | 7.20 |

The technology according to the invention (TS1 solution (polyglycerol succinic ester from example 1)) shows a color retention effect with lower color loss Delta E than for the control.

Post-Treatment Benefits

Post-treatment by polyglycerol succinic ester from example 1 kept the original color darkness with almost no change in L*.

|  | Initial Color L*, a*, b* | | |
|---|---|---|---|
|  | L* | a* | b* |
| Hair without treatment | 24.15 | 27.03 | 15.14 |
| TS1 (polyglycerol succinic ester from example 1) | 24.46 | 21.7 | 11.12 |

Color Retention Benefit for Post-Treatment

|  | Color Loss Delta E |
|---|---|
| Control | 17.91 |
| TS1 (polyglycerol succinic ester from example 1) | 5.28 | shows a color retention effect with lower color loss Delta E than for the control.

Post-treatment by the technology according to the invention (TS1 solution (polyglycerol succinic ester from example 1)) reduced the color loss Delta E by more than 12 units.

Example 7.2 Post Bleach Treatment 4 gram undamaged Dark brown hair tresses were obtained from Hair International Importers. A commercial bleaching lightener powder (9 grams) and a commercial 40 volume developer (11 grams) were mixed together. The bleaching composition was applied to the virgin dark brown hair tress, spread through and left on the hair tress for 50 min. After rinsing the dye from the tress with tap water, the tress was washed with a 10 wt % Sodium Laureth Sulfate (2 EO) solution and rinsed. The dried hair was immersed in 50 g TS1 solution for 30 minutes. Then the hair was dried at room temperature overnight. The hair bundle was then washed by 10 wt-% SLES (Sodium Lauryl Ether Sulfate) for 3 times. Hair was then dried.

This treatment is to strengthen the hair after bleaching.

Example 7.3: White Rinse Off Conditioner Formulation

| Part | Chemical Name | wt % |
|---|---|---|
| A | Water | q.s. to 100 |
|  | Lactic Acid | 0.6 |
| B | Amidet APA-22 (Behenamidopropyl Dimethylamine) from Kao Corporation | 2.2 |
| C | Kalcol 6850 (Cetostearyl alcohol) from Kao Corporation | 4.4 |
| D | polyglycerol succinic ester from example 1 30% solution in dipropylene glycol | 7 |

1. Part A. Lactic acid and water were mixed and heated to 80° C.

2. Part B was added to part A and the mixture stirred for 1-3 hours at 80° C. to provide a homogeneous formulation.

3. Part C was added to the mixture of A and B and stirred at 80° C. for 0.5 to 1 hour until Part C was completely molten and a homogeneous mixture was obtained.

4. The heating source was removed while stirring continued until room temperature was reached.

5. Part D was added to the mixture consisting of A+B+C and stirring continued until a homogeneous mixture was reached.

Example 7.4. Pearlescent Shampoo Formulation

| Part | Component | wt % |
|---|---|---|
| A | Sodium Laureth Sulfate | 12 |
|  | Cocamidopropyl Betaine | 3 |
| B | Ethylene Glycol Distearate | 1 |
|  | Water | 10 |
| C | Cocamide Monoethanolamide | 1 |
|  | Water | 10 |
| D | Polyquaternium-6 | 0.06 |
|  | ACULYN™ 38 from the Dow Chemical Company (10 wt-% active) | 3 |
| E | polyglycerol succinic ester from example 1 30% solution in dipropylene glycol | 7 |
| F | Water | q.s. to 100 |

Part A: The components of part A were mixed with an overhead mechanical stirrer at 600 rpm for 10 minutes.

Part B: 1 g ethylene glycol distearate and 10 g water were mixed with a magnetic stirrer at 200 rpm for 15 minutes.

Part C: 1 g cocamide monoethanolamide and 10 g water were mixed with a magnetic stirrer at 200 rpm for 15 minutes.

The components of part D were added to part A and stirred with an overhead mechanical stirrer at 600 rpm for 10 minutes. A mixture A+D was obtained.

Part B was added to the mixture A+D and stirred for 10 minutes at 600 rpm with a mechanical stirrer. Mixture A+D+B was obtained.

Part C was added to the mixture A+D+B and stirred for 10 minutes at 600 rpm with a mechanical stirrer. Mixture A+D+B+C was obtained.

Part E was added to the mixture A+D+B+C and stirred for 15 minutes at 600 rpm with a mechanical stirrer. Mixture A+D+B+C+E was obtained.

Part F was added last to the mixture A+D+B+C+E and the mixture stirred for 15 minutes at 600 rpm with a mechanical stirrer.

Example 7.5: Pearlescent Shampoo Non-Sulfate Version

| Part | Component | Wt % |
|---|---|---|
| A | Sodium Lauryl Sulfoacetate + | 10.6 |
|   | Disodium Laureth Sulfosuccinate |  |
|   | Cetyl Betaine | 3.3 |
| B | Cocamide Monoethanolamide | 1.5 |
|   | Water | 10 |
| C | Hydroxypropyl Methylcellulose | 1.5 |
|   | Water | 10 |
| D | Ethylene Glycol Distearate | 1.5 |
|   | Water | 10 |
| E | Polyquaternium-10 | 0.15 |
| F | polyglycerol succinic ester from example 1 30% solution in dipropylene glycol | 7 |
| G | Water | q.s. to 100 |

Part A: The components of part A were mixed with an overhead mechanical stirrer at 600 rpm for 10 minutes.

Part B: 1.5 g cocamide monoethanolamide was mixed with 10 g water (45° C.) with a magnetic stirrer at 200 rpm for 30 minutes.

Part C: 1.5 g hydroxypropyl methylcellulose powder was slowly added to 10 g water (45° C.) and stirred with a magnetic stirrer at 200 rpm for 30 minutes.

Part D: 1.5 g ethylene glycol distearate powder was slowly added to 10 g water (45° C.) and stirred with a magnetic stirrer at 200 rpm for 30 minutes.

Part B was slowly added to part A with mechanical stirring at 600 rpm for 5 minutes. Mixture A+B was obtained.

Part C was slowly added to part A+B with mechanical stirring at 600 rpm for 5 minutes. Mixture A+B+C was obtained.

Part D was slowly added to part A+B+C with mechanical stirring at 600 rpm for 5 minutes. Mixture A+B+C+D was obtained.

Part E was added to part A+B+C+D with mechanical stirring at 600 rpm for 10 minutes. Mixture A+B+C+D+E was obtained.

Part F was added to the mixture A+B+C+D+E and mechanically stirred for 15 minutes at 600 rpm.

Finally, Part G was added and the mixture stirred at 600 rpm for 30 minutes.

Example 7.6: Anti-Frizz Shampoo

| Part | Component | wt % |
|---|---|---|
| A | Water | 55 |
|   | PEG-120 Methyl Glucose Dioleate | 2 |
| B | Water | 15.25 |
|   | Sodium Laureth Sulfate | 9 |
| C | Dissodium EDTA | 0.1 |
|   | Cocamidopropyl Betaine | 10 |
|   | Polyquaternium-7 | 0.5 |
|   | Decyl Glucoside | 1 |
|   | Dexpanthenol | 1 |
|   | Phenoxyethanol | 0.5 |
| D | polyglycerol succinic ester from example 1 30% solution in dipropylene glycol | 7 |
|   | Tropicalism 18 from Givaudan S.A. | 0.65 |

Part A: The components of part A were mixed with a magnetic stirrer at 200 rpm for 15 minutes.

Part B: The components of part B were mixed with a magnetic stirrer at 200 rpm for 15 minutes.

Part B was added to part A and the mixture stirred with an overhead mechanical stirrer at 500 rpm for 15 minutes.

The Components of part C were added to the mixture A+B and stirred with an overhead mechanical stirrer at 500 rpm for 1 hour.

The components of part D were mixed with a magnetic stirrer at 200 rpm for 15 minutes and afterwards added to the mixture A+B+C.

Finally, the complete mixture A+B+C+D was mixed with a mechanical stirrer at 500 rpm for 30 minutes.

Example 7.7: Water Based Spray Formulation 1.5 wt % polyglycerol succinic ester from example 1

3.5 wt % dipropylene glycol, 1.25 wt % SLES, 0.09 wt % NaOH (added as a 10 wt % active NaOH solution in water of pH 8)

Water q.s. to 100 wt %

Example 7.8: Isopropanol (IPA) Based Spray Formulation 1.5 wt % polyglycerol succinic ester from example 1

3.5 wt % dipropylene glycol

IPA q.s. to 100%

Example 8: Treatment Gel and Cream Formulations

Example 8.1

| Ingredients | Formulation | | | | |
| --- | --- | --- | --- | --- | --- |
| | 1 Wt % | 2 wt | 3 Wt % | 4 Wt % | 5 Wt % |
| Carbopol 1382 | 1 | 1 | | | |
| Xanthan gum | 0.1 | 0.1 | 0.5 | | |
| Hydroxypropyl starch phosphate | | | | 4 | |
| Hydroxyethyl cellulose | | | | | 1 |
| polyglycerol succinic ester from example 1 | 10 | 10 | 10 | 10 | 5 |
| Dipropylene glycol | 30 | | | | |
| Butylene glycol | | | 30 | | 30 |
| isopropanol | 25 | | 25 | | 25 |
| water | q.s 100 | q.s 100 | q.s 100 | q.s 100 | q.s 100 |
| NaOH 10% | q.s pH 4 | q.s pH 7 | q.s pH 6.5 | q.s pH 6.5 | q.s pH 6.5 |

Example 8.2

| Ingredients | Wt % |
| --- | --- |
| Phospholipids (and) *glycine soja* oil | 2 |
| propanediol | 3 |
| polyglycerol succinic ester from example 1 | 10 |
| Sodium acrylates copolymer and lecithin | 1.7 |
| Stearic acid | 0.5 |
| Behenyl alcohol | 0.5 |
| Isononyl isononaote | 2 |
| Glycerin and *picea abies* extract and alcohol | 1 |
| phenoxyethanol | 0.5 |
| Butylene glycol dicaprylate/dicaprate | 2 |
| water | q.s to 100 |

Example 9

A Glycerol Diglycidyl Ether Based Tartaric Acid Ester Derivative

In a 100 ml three-necked flask, equipped with refluxing condenser, thermometer and magnetic stirrer, 15 g (146.9 mmol epoxy groups) of glycerol diglycidylether, 22.05 g (146.9 mmol) tartaric acid, 0.56 g trimethylamine and 86.45 g dipropylene glycol are mixed and heated to 90° C. for 12 hrs. Afterwards, the mixture is cooled to room temperature and the conversion of the epoxide groups determined by means of $^1$H NMR spectroscopy. The conversion epoxy groups is 100%.

A colorless product essentially consisting of the following isomers:

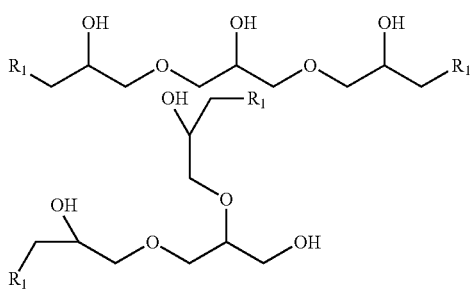

with
$R_1$ being —OC(O)CH(OH)CH(OH)C(O)OH
is obtained.

Example 10

Glycerol Dig Lycidyl Ether Based N-Acetyl Aspartic Acid Ester Derivative

In a 100 ml three-necked flask, equipped with refluxing condenser, thermometer and magnetic stirrer, 5 g (48.9 mmol epoxy groups) of glycerol diglycidylether, 8.58 g (48.9 mmol) N-acetyl aspartic acid:

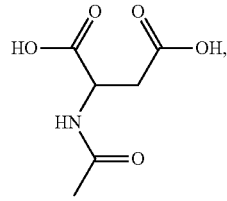

0.2 g trimethylamine and 54.3 g 1,3-butanediol are mixed and heated to 90° C. for 10 hrs. Afterwards, the mixture is cooled to room temperature and the conversion of the epoxide groups determined by means of $^1$H NMR spectroscopy. The conversion epoxy groups is 100%.

A slightly yellowish product essentially consisting of the following isomers is obtained:

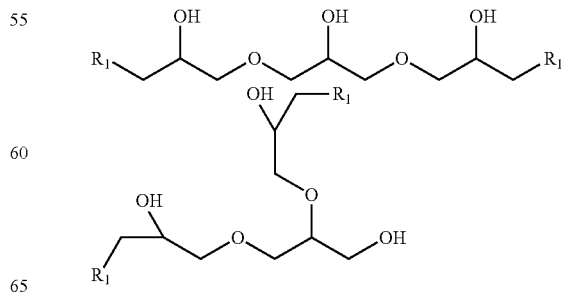

with
R$_1$ being —OC(O)CH$_2$CH(R*)C(O)OH or —OC(O)CH(R*)CH$_2$C(O)OH, wherein
R*=—NH(CO)CH$_3$.

Example 11

N-Maleoyl-β-alanine ((E)-4-(2-carboxyethylamino)-4-oxo-but-2-enoic acid)

In a 100 ml three-necked flask, equipped with refluxing condenser, thermometer and magnetic stirrer, 17.8 g (200 mmol) of β-alanine are dissolved in 40 g DI water at room temperature. 19.6 g (200 mmol) of maleic acid anhydride are added. The temperature increases from 22 to 36° C. within 20 minutes. The mixture turns into a turbid white dispersion. The temperature is adjusted at 22° C. for 3 hrs. Afterwards, the precipitate is filtered, washed 10× with 20 ml DI water and 3× with 20 ml cyclohexane. Finally, the volatiles are removed at 40° C./20 mm Hg. The structure of the material was confirmed by means of $^1$H NMR spectroscopy.

22 g of a white powder essentially consisting of the following structure are obtained.

N-Maleoyl-β-alanine ((E)-4-(2-carboxyethylamino)-4-oxo-but-2-enoic acid)

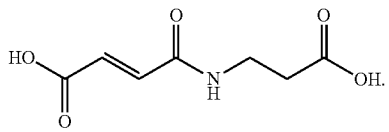 [SMILES: O=C(O)/C=C/C(=O)NCCC(=O)O]

Example 12

Glycerol Diglycidyl Ether Based Derivative of N-Maleoyl β-Alanine

In a 100 ml three-necked flask, equipped with refluxing condenser, thermometer and magnetic stirrer, 10 g (53.4 mmol) of the N-maleoyl β-alanine according to example 11, 60 g 1,3-butanediol and 0.23 g trimethylamine are mixed at room temperature and heated to 70° C. 5.45 g (53.4 mmol epoxy groups) of glycerol diglycidylether are added. The mixture is heated to 90° C. for 12 hrs. The mixture turns transparent during the heating process. Afterwards, the mixture is cooled to room temperature and the conversion of the epoxide groups determined by means of $^1$H NMR spectroscopy. The conversion epoxy groups is 100%.

A reddish product essentially consisting of the following isomers is obtained:

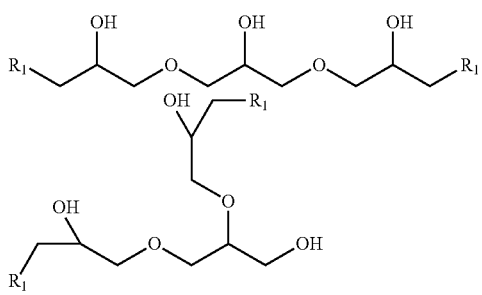

with
R$_1$ being —OC(O)CH=CHC(O)NHCH$_2$CH$_2$C(O)OH or —OC(O)CH$_2$CH$_2$NHC(O)CH=CHC(O)OH.

Example 13

N-Maleoyl-asparagine (4-amino-2-[[(E)-4-hydroxy-4-oxo-but-2-enoyl]amino]-4-oxo-butanoic acid)

In a 100 ml three-necked flask, equipped with refluxing condenser, thermometer and magnetic stirrer, 26.42 g (200 mmol) of asparagine are dispersed in 46 g DI water at room temperature. 19.6 g (200 mmol) of maleic acid anhydride are added. The mixture forms a white dispersion which is stirred at 23° C. for 5 hrs. Afterwards, the mixture is heated to 50° C. for 5.5 hrs. It forms a transparent solution. Volatiles are removed at 45° C./20 mm Hg. The sticky residue is twice washed with 2-propanol and volatile components removed at 45° C./20 mmHg. The structure of the material was confirmed by means of $^1$H NMR spectroscopy.

A colorless candy like material essentially consisting of the following structure is obtained

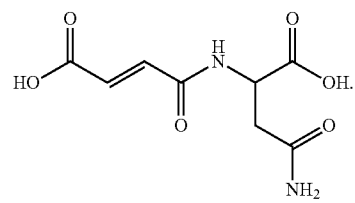 [SMILES: NC(=O)CC(NC(=O)/C=C/C(=O)O)C(=O)O]

Example 14

Glycerol Diglycidyl Ether Based Derivative of N-Maleoyl Asparagine

In a 100 ml three-necked flask, equipped with refluxing condenser, thermometer and magnetic stirrer, 12.29 g (53.4 mmol) of the N-maleoyl asparagine according to example 13, 60 g 1,3-butanediol and 0.27 g trimethylamine are mixed at room temperature and heated to 70° C. 5.45 g (53.4 mmol epoxy groups) of glycerol diglycidylether are added. The mixture is heated to 90° C. for 12 hrs. A white dispersion is formed during the heating process. Afterwards, the mixture is cooled to room temperature and the conversion of the epoxide groups determined by means of $^1$H NMR spectroscopy. The conversion epoxy groups is >99%.

A white dispersion essentially consisting of the following isomers is obtained:

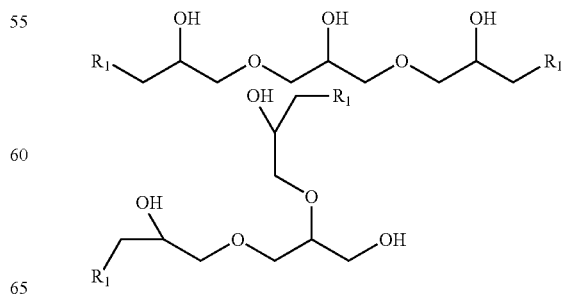

with $R_1$ being —OC(O)CH=CHC(O)NHCH(CH$_2$C(O)NH$_2$)C(O)OH or —OC(O)CH(CH$_2$C(O)NH$_2$)NHC(O)CH=CHC(O)OH.

The material is instantaneously soluble in DI water.

APPLICATIONS EXAMPLES

Example 15

Application on Color Enhancement and Color Retention of Single Bleached European Hair The following treatment solution was prepared:

TS2 solution (glycerol diglycidyl ether based tartaric acid ester derivative from example 9) approximately 50 ml was composed of the glycerol diglycidyl ether based tartaric acid ester from example 9 3 g, 7 g 1,3 butanediol (that is 10 g solution of the glycerol diglycidyl ether based tartaric acid ester in 1,3 butanediol obtained in example 9), and 40 g water.

TS3 solution (glycerol diglycidyl ether based N-acetyl aspartic acid ester derivative from Example 10) approximately 50 ml was composed of the glycerol diglycidyl ether based N-acetyl aspartic acid ester from example 10 3 g, 12 g 1,3 butanediol (that is 15 g solution of the glycerol diglycidyl ether based tartaric acid ester in 1,3 butanediol obtained in example 10), and 35 g water.

TS4 solution (glycerol diglycidyl ether based derivative of N-maleoyl β-alanine from Example 12) approximately 50 ml was composed of the glycerol diglycidyl ether based derivative of N-maleoyl β-alanine from example 12 3 g, 12 g 1,3 butanediol (that is 15 g solution of the glycerol diglycidyl ether based derivative of N-maleoyl β-alanine in 1,3 butanediol obtained in example 12), and 35 g water.

The hair dye was a commercial hair dye Garnier Nutrisse Ultra Color R3, Light Intense Auburn, from L'Oreal.

Post-Treatment with the Aqueous Solution According to Invention after the Dyeing Step A bundle of 4 g single bleached European hair tress (Kerling International Haarfarbrik GmbH) dyed with Garnier R3 dye for 30 minutes following the standard dyeing procedure of Garnier R3. Then the hair was dried by bonnet. The initial color was measured. The dried hair was immersed in 50 g TS2 solution or TS3 solution or TS4 solution for 30 minutes. Then the hair was dried at room temperature overnight. The hair bundle was then washed by 10 wt-% SLES (Sodium Lauryl Ether Sulfate) for 3 times. Hair was then dried.

The control tress was Garnier R3 dyed tress treated by 50 ml water. The hair was then washed with 10 wt-% SLES and dried same as hair tress treated by crosslinking technology.

Wash Protocol

The 4 g hair tresses were put in 250 ml conical flask with 200 ml 2.5% SLES solution. The flask was shaken at 120 rpm 42° C. in Shel Lab shaking water bath for 5 minutes, (5 minutes wash equals 10 hand washes.) After 5 minutes, the hair was dried and the hair color was measured.

Post-Treatment Benefits

Color Enhancement (Deepening) for the TS2 Post-Treatment

|  | Before Wash Color L*, a*, b* | | | Color Enhancement |
| --- | --- | --- | --- | --- |
|  | L* | a* | b* | Delta E |
| Before Treatment of TS2 | 26.74 | 29.75 | 17.74 |  |
| After TS2 Treatment (glycerol diglycidyl ether based tartaric acid ester derivative from example 9) | 23.62 | 15.20 | 6.70 | 18.53 |

TS2 notably deepens the hair color tone upon a post-treatment protocol.

The TS3 and TS4 treatments do not deepen the color tone.

|  | Before Wash Color L*, a*, b* | | |
| --- | --- | --- | --- |
|  | L* | a* | b* |
| Before Treatment of TS3 | 26.83 | 30.23 | 18.18 |
| After TS3 Treatment (glycerol diglycidyl ether based N-acetyl aspartic acid ester derivative from Example 10) | 27.33 | 24.78 | 14.27 |
| Before Treatment of TS4 | 26.89 | 30.08 | 18.16 |
| After TS4 Treatment (glycerol diglycidyl ether based derivative of N-maleoyl β-alanine from Example 12) | 28.29 | 26.45 | 15.42 |

Color Retention Benefit for Post-Treatment

|  | Color Loss Delta E |
| --- | --- |
| Control | 17.91 |
| TS2 (glycerol diglycidyl ether based tartaric acid ester derivative from example 9) | 10.35 |
| TS3 (glycerol diglycidyl ether based N-acetyl aspartic acid ester derivative from Example 10) | 7.73 |
| TS4 (glycerol diglycidyl ether based derivative of N-maleoyl β-alanine from Example 12) | 7.93 |

The above table on the post-treatment results shows that TS2, TS3 and TS4 provide significant and visible color loss benefits over the control. While TS3 and TS4 provided color loss Delta E improvements of about 10 against the control, TS2 provided a color loss Delta E improvement of about 7.5.

Example 16

A Silicone Based Tartaric Acid Ester Derivative (Terminal)

In a 100 ml three-necked flask, equipped with refluxing condenser, thermometer and magnetic stirrer, 15 g (39.7 mmol epoxy groups) of a silicone diepoxide of the structure

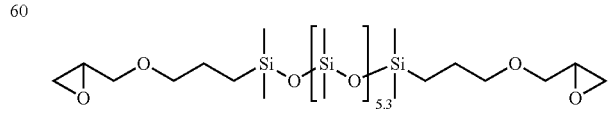

5.96 g (39.7 mmol) tartaric acid, 0.31 g trimethylamine and 48.9 g 1,3-butanediol are mixed at room temperature under N₂. The mixture is heated to 90° C. for 11 hours. Afterwards, the mixture is cooled to room temperature and the conversion of the epoxide groups determined by means of ¹H NMR spectroscopy. The conversion epoxy groups is 99%.

A colorless product essentially consisting of the following structure is obtained:

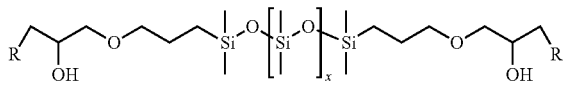

with
x=5.3, and
R being —OC(O)CH(OH)CH(OH)C(O)OH.

Example 17

A Silicone Based N-Acetyl Aspartic Acid Ester Derivative

In a 100 ml three-necked flask, equipped with refluxing condenser, thermometer and magnetic stirrer, 10 g (26.5 mmol epoxy groups) of a silicone diepoxide of the structure

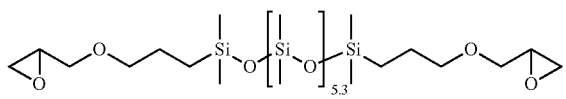

4.64 g (26.5 mmol)N-acetyl aspartic acid, 0.22 g trimethylamine and 58.6 g 1,3-butanediol are mixed at room temperature under N₂. The mixture is heated to 90° C. for 10 hours. Afterwards, the mixture is cooled to room temperature and the conversion of the epoxide groups determined by means of ¹H NMR spectroscopy. The conversion epoxy groups is 100%.

A brownish product essentially consisting of the following structure is obtained:

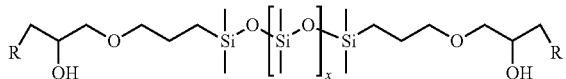

with
x=5.3, and
R being —OC(O)CH₂CH(R*)C(O)OH or —OC(O)CH(R*)CH₂C(O)OH, wherein
R*=—NH(CO)CH₃.

Example 18

A Silicone Based Derivative of N-Maleoyl β-Alanine

In a 100 ml three-necked flask, equipped with refluxing condenser, thermometer and magnetic stirrer, 10 g (26.5 mmol epoxy groups) of a silicone diepoxide of the structure

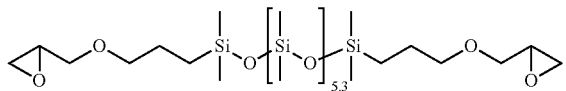

4.95 g (26.5 mmol)N-maleoyl β-alanine according to example 11, 0.23 g trimethylamine and 60 g 1,3-butanediol are mixed at room temperature under N₂. The mixture is heated to 90° C. for 12 hours. Afterwards, the mixture is cooled to room temperature and the conversion of the epoxide groups determined by means of ¹H NMR spectroscopy. The conversion epoxy groups is 100%.

A reddish product essentially consisting of the following structure is obtained

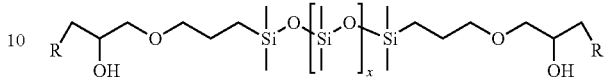

with
x=5.3 and
R being —OC(O)CH=CHC(O)NHCH₂CH₂C(O)OH or —OC(O)CH₂CH₂NHC(O)CH=CHC(O)OH.

The invention claimed is:

1. A compound (B)
which is selected from the group consisting of:
a compound of the formula:

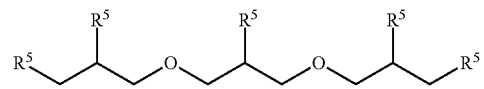

wherein R⁵ is selected from the group consisting of hydroxy and F, wherein F is
F is selected from:

—O—C(O)—R³—C(O)OH, and

—NR¹—C(O)—R³—C(O)OH, where R³ is selected from a single bond or optionally substituted straight-chain, cyclic, branched, saturated, unsaturated, and aromatic hydrocarbon radicals which have up to 100 carbon atoms, which optionally contain one or more groups selected from —O—, —NH—, —C(O)—, —C(S)—, tertiary amino groups

and quaternary ammonium groups

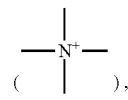

with the proviso that R³ is not —CH=CH—,
with the proviso that at least two of R⁵ are F;
a compound of the formula:

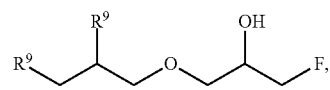

wherein one of R⁹ is hydroxy and one of R⁹ is a group of the formula

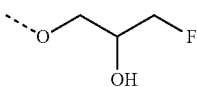

and wherein F is as defined above and the dotted line is the bond to the carbon atom;

a mixture of the following two isomers:

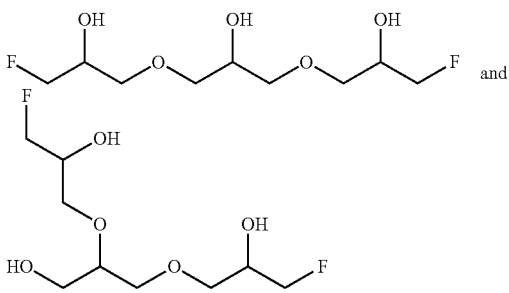

wherein F is as defined above; and, a compound of the formula:

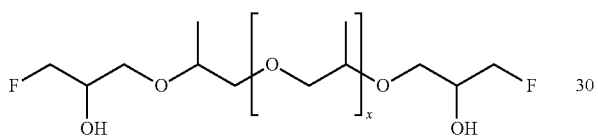

wherein x is from 1 to 10, and F is as defined above.

2. A compound according to claim 1, wherein $R^3$ is selected from the group consisting of a single bond, and straight-chain, cyclic, branched, saturated, unsaturated and aromatic hydrocarbon radicals which have up to 18 carbon atoms, and which optionally contain one or more groups selected from —O—, —NH—, —C(O)—, and wherein $R^3$ is optionally substituted by one or more groups selected from hydroxyl groups, amino groups, and carboxy groups.

3. A compound according to claim 1, wherein $R^3$ is derived from a dicarboxylic acid of the formula:

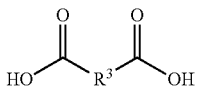

wherein $R^3$ is as defined above, and is optionally substituted aliphatic, saturated or unsaturated or aromatic dicarboxylic acids selected from the group consisting of oxalic acid (ethanedioic acid), malonic acid (propanedioic acid), succinic acid (butanedioic acid), glutaric acid (pentanedioic acid), adipic acid (hexanedioic acid), pimelic acid (heptanedioic acid), suberic acid (octanedioic acid), azelaic acid (nonanedioic acid), sebacic acid (decanedioic acid), undecanedioic acid, dodecanedioic acid, brassylic acid (tridecanedioic acid), thapsic acid (hexadecanedioic acid), glutaconic acid (pent-2-enedioic acid), citraconic acid ((2Z)-2-methylbut-2-enedioic acid), mesaconic acid ((2E)-2-methyl-2-butenedioic acid), itaconic acid (2-methylidenebutanedioic acid), tartronic acid (2-hydroxypropanedioic acid), mesoxalic acid (oxopropanedioic acid), malic acid (hydroxybutanedioic acid), tartaric acid (2,3-dihydroxybutanedioic acid), oxaloacetic acid (oxobutanedioic acid), aspartic acid (2-aminobutanedioic acid), α-hydroxy glutaric acid (2-hydroxypentanedioic acid), arabinaric acid (2,3,4-trihydroxypentanedioic acid), acetonedicarboxylic acid (3-oxopentanedioic acid), α-ketoglutaric acid (2-oxopentanedioic acid), glutamic acid (2-aminopentanedioic acid), diaminopimelic acid ((2R,6S)-2,6-diaminoheptanedioic acid), saccharic acid ((2S,3S,4S,5R)-2,3,4,5-tetrahydroxyhexanedioic acid), phthalic acid (benzene-1,2-dicarboxylic acid), isophthalic acid (benzene-1,3-dicarboxylic acid), terepthtalic acid ((benzene-1,3-dicarboxylic acid)), diphenic acid (2-(2-carboxyphenyl)benzoic acid), 2,6-naphthalenedicarboxylic acid, norbornene dicarboxylic acid, norbornane dicarboxylic acid, and trimellitic acid, or $R^3$ is derived from an aliphatic or aromatic tricarboxylic acid, wherein $R^3$ is substituted with carboxyl group (COOH) and is selected from the group consisting of citric acid (2-hydroxypropane-1,2,3-tricarboxylic acid), isocitric acid (1-hydroxypropane-1,2,3-tricarboxylic acid), aconitic acid ((cis or trans prop-1-ene-1,2,3-tricarboxylic acid), propane-1,2,3-tricarboxylic acid; trimesic acid (benzene-1,3,5-tricarboxylic acid), the reaction products of carboxylic acid anhydrides selected from the group consisting of maleic anhydride and succinic anhydride, with amino acids and amino acid derivatives, selected from the group consisting of b-alanine and asparagine, and which are selected from the group consisting of N-acetyl aspartic acid, N-maleoyl-β-alanine ((E)-4-(2-carboxyethylamino)-4-oxobut-2-enoic acid), and N-maleoyl-asparagine (4-amino-2-[[(E)-4-hydroxy-4-oxo-but-2-enoyl]amino]-4-oxobutanoic acid).

4. A compound according to claim 1, wherein F is selected from the group consisting of the formulas:

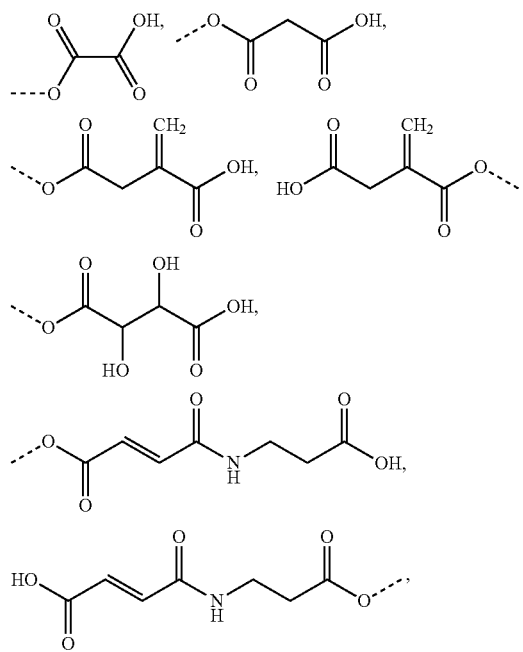

-continued
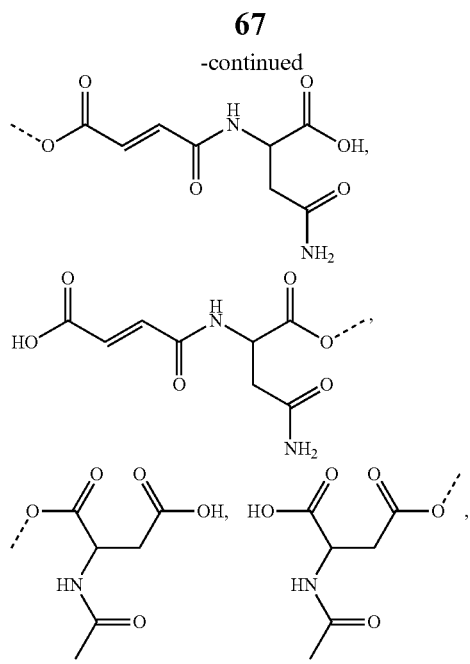
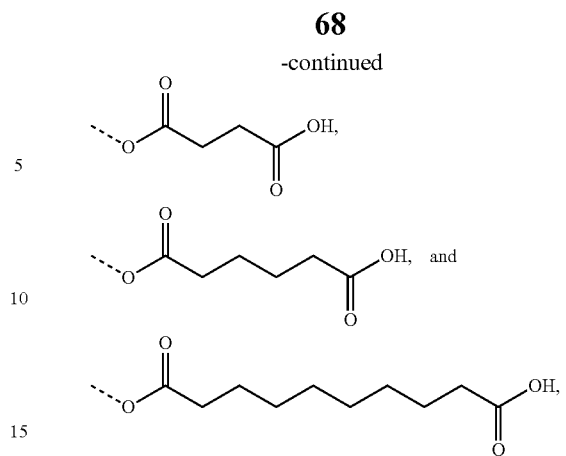
wherein the dotted line in the above formulae represents the bond to the oxygen atom, and wherein there are at least two groups F.
5. The compound of claim 1 which has the formula:
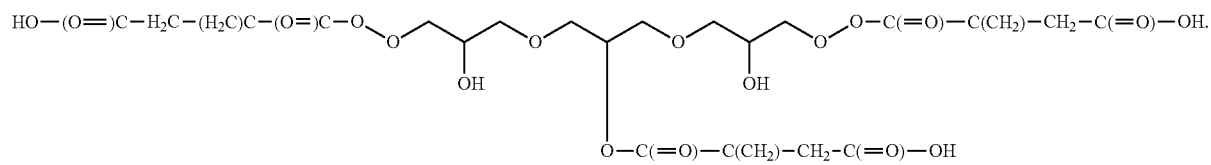
* * * * *